United States Patent [19]
Sauer

[11] Patent Number: 6,109,264
[45] Date of Patent: Aug. 29, 2000

[54] APPARATUS FOR EXPANDING BODY TISSUE

[75] Inventor: Jude S. Sauer, Pittsford, N.Y.

[73] Assignee: LaserSurge, Inc., Rochester, N.Y.

[21] Appl. No.: 08/838,185

[22] Filed: Apr. 16, 1997

Related U.S. Application Data

[63] Continuation-in-part of application No. 08/592,056, Jan. 26, 1996, Pat. No. 5,690,669
[60] Provisional application No. 60/015,785, Apr. 17, 1996.

[51] Int. Cl.[7] ................................................. A61M 16/00
[52] U.S. Cl. .............................. 128/207.29; 128/200.26
[58] Field of Search ........................ 128/200.24, 200.26, 128/207.14, 207.29; 604/117, 187, 212

[56] References Cited

U.S. PATENT DOCUMENTS

| | | | |
|---|---|---|---|
| 3,635,218 | 1/1972 | Ericson | 604/212 |
| 4,239,042 | 12/1980 | Asai | 128/207.29 |
| 4,278,081 | 7/1981 | Jones | 128/207.15 |
| 4,324,235 | 4/1982 | Beran | 128/207.15 |
| 4,340,046 | 7/1982 | Cox | 128/207.17 |
| 4,364,391 | 12/1982 | Toye | 128/207.29 |
| 4,449,523 | 5/1984 | Szachowicz et al. | 128/200.26 |
| 4,459,984 | 7/1984 | Liegner | 128/207.15 |
| 4,471,776 | 9/1984 | Cox | 128/207.15 |
| 4,475,906 | 10/1984 | Holzner | 604/187 |
| 4,488,545 | 12/1984 | Shen | 128/207.29 |
| 4,573,460 | 3/1986 | Szachowicz et al. | 128/200.26 |
| 4,677,978 | 7/1987 | Melker | 128/207.14 |
| 4,801,293 | 1/1989 | Jackson | 604/117 |
| 4,802,479 | 2/1989 | Haber et al. | 606/192 |
| 4,832,692 | 5/1989 | Box et al. | 604/99 |
| 4,877,021 | 10/1989 | Higer et al. | 128/200.26 |
| 4,889,112 | 12/1989 | Schachner et al. | 128/207.29 |
| 4,976,725 | 12/1990 | Chin et al. | 606/192 |
| 5,045,061 | 9/1991 | Seifert et al. | 604/96 |
| 5,054,484 | 10/1991 | Hebeler, Jr. | 128/207.16 |
| 5,055,107 | 10/1991 | Lester | 128/207.29 |
| 5,056,515 | 10/1991 | Abel | 128/207.15 |
| 5,058,580 | 10/1991 | Hazard | 128/207.15 |
| 5,062,420 | 11/1991 | Levine | 128/204.18 |
| 5,084,060 | 1/1992 | Freund et al. | 606/192 |
| 5,090,408 | 2/1992 | Spoffard et al. | 128/207.14 |
| 5,147,300 | 9/1992 | Robinson et al. | 604/97 |
| 5,181,509 | 1/1993 | Spoffard et al. | 128/207.14 |
| 5,186,168 | 2/1993 | Spoffard et al. | 128/207.29 |
| 5,188,630 | 2/1993 | Christoudias | 606/1 |
| 5,209,731 | 5/1993 | Sterman et al. | 604/97 |
| 5,217,005 | 6/1993 | Weinstein | 128/207.29 |
| 5,217,007 | 6/1993 | Ciaglia | 128/207.29 |

(List continued on next page.)

FOREIGN PATENT DOCUMENTS

| | | | |
|---|---|---|---|
| WO91/07202 | 5/1991 | WIPO | 128/207.29 |
| WO91/08709 | 6/1991 | WIPO | 128/207.29 |

OTHER PUBLICATIONS

Insertion Forces and Risk of Complications During Cricothyroid Cannulation—Original Contributions/The Journal of Emergency Medicine, vol. 10, pp. 417–426, 1992, Copyright 1992 Permagon Press Ltd.

4th World Congress of Endoscopic Surgery: Abstracts Surg. Endosc (1994) 8: 429–596. Copyright Springer–Verlag New York Inc. 1994.

*Primary Examiner*—Aaron J. Lewis
*Attorney, Agent, or Firm*—Harter, Secrest & Emery LLP; Brian B. Shaw, Esq.; Stephen B. Salai, Esq.

[57] ABSTRACT

A surgical apparatus for manipulating body tissue including a hollow needle, a bulb connected to the needle for aspirating air through an end of the needle, a flexible guide wire extending through the needle, a fitting on one end of the guide wire for permitting the guide wire to be reciprocated with the same hand that holds the instrument, from a retracted position substantially within the needle, to an extended position in which a substantial length of the guide wire extends beyond an end of the needle, an expandable dilator attached to the dilation tip for dilating a tracheal wall when the dilator is inflated, and a tracheostomy tube detachably mounted with respect to the dilator for placement into a lumen of a trachea.

24 Claims, 20 Drawing Sheets

U.S. PATENT DOCUMENTS

| | | | |
|---|---|---|---|
| 5,217,008 | 6/1993 | Lindholm | 128/207.14 |
| 5,235,970 | 8/1993 | Augustine | 128/200.26 |
| 5,279,285 | 1/1994 | Griggs | 128/200.26 |
| 5,284,480 | 2/1994 | Porter et al. | 604/97 |
| 5,290,257 | 3/1994 | Zhong | 604/187 |
| 5,304,147 | 4/1994 | Johnson et al. | 604/183 |
| 5,306,147 | 4/1994 | Dragan et al. | 433/90 |
| 5,322,062 | 6/1994 | Servas | 128/207.14 |
| 5,336,201 | 8/1994 | Von der Decken | 604/223 |
| 5,352,206 | 10/1994 | Cushieri et al. | 604/164 |
| 5,389,077 | 2/1995 | Melinyshyn et al. | 604/117 |
| 5,507,279 | 4/1996 | Fortune et al. | 128/207.29 |
| 5,507,301 | 4/1996 | Wasicek | 606/192 |
| 5,690,669 | 11/1997 | Sauer et al. | 606/192- |

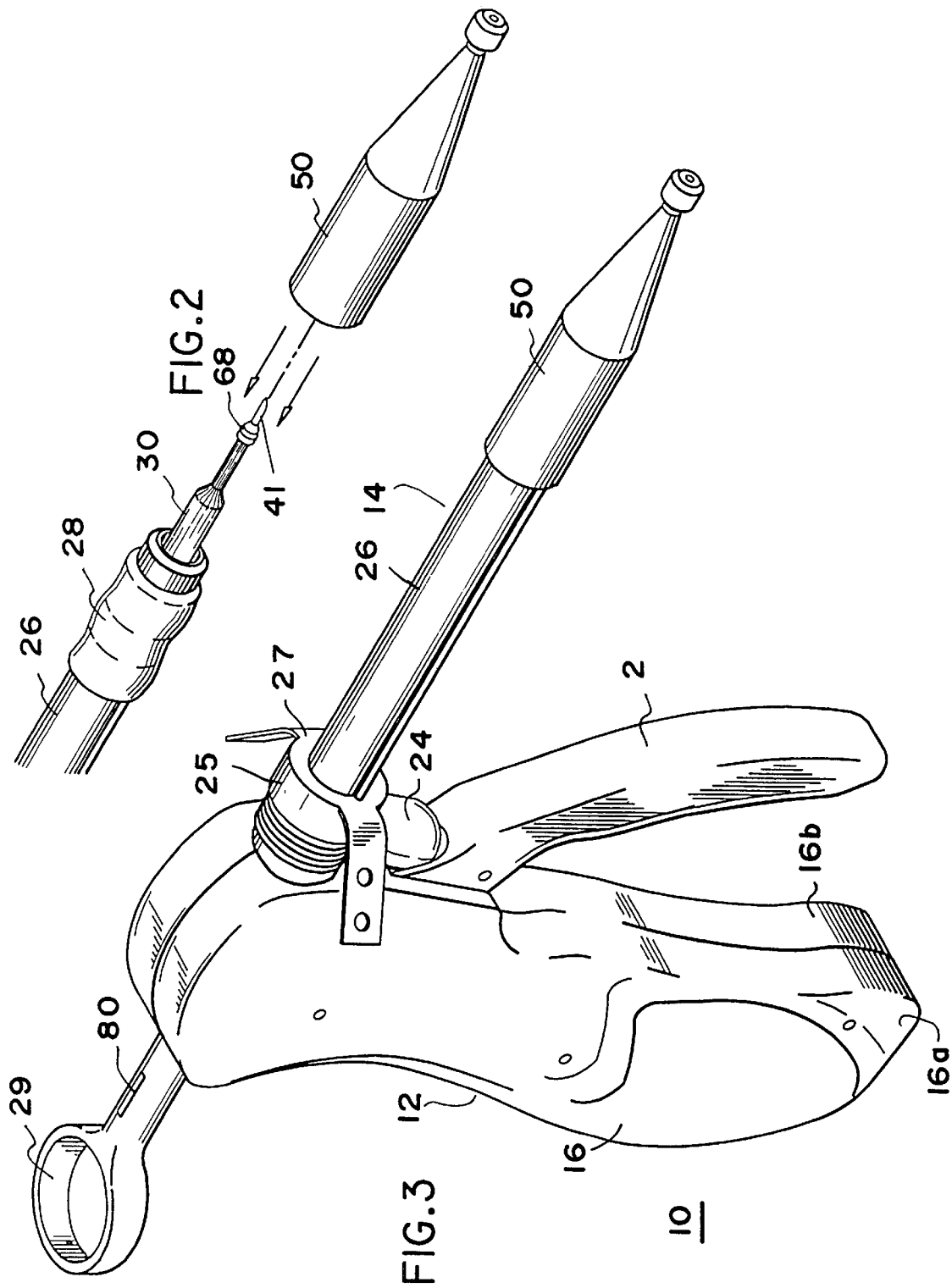

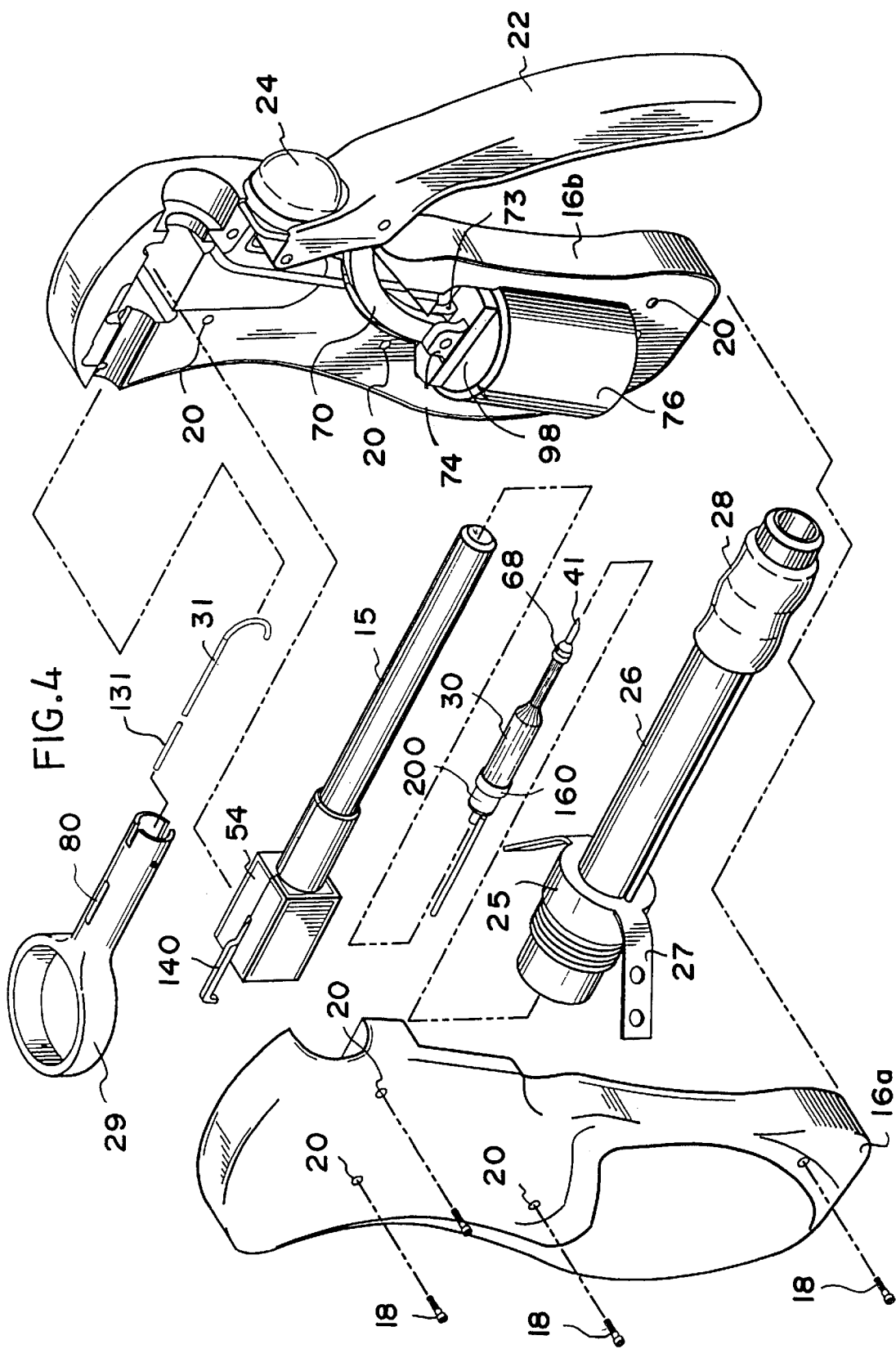

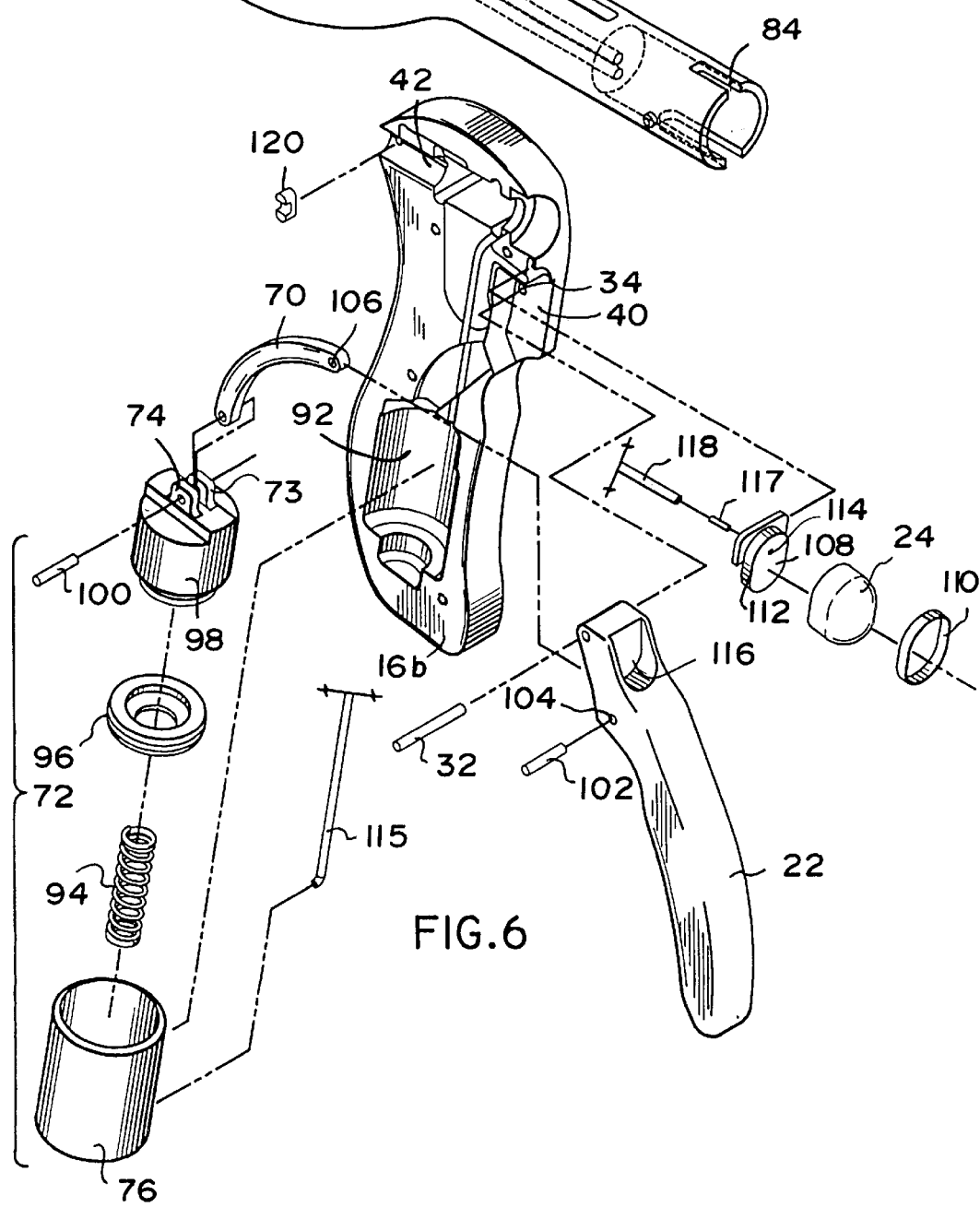

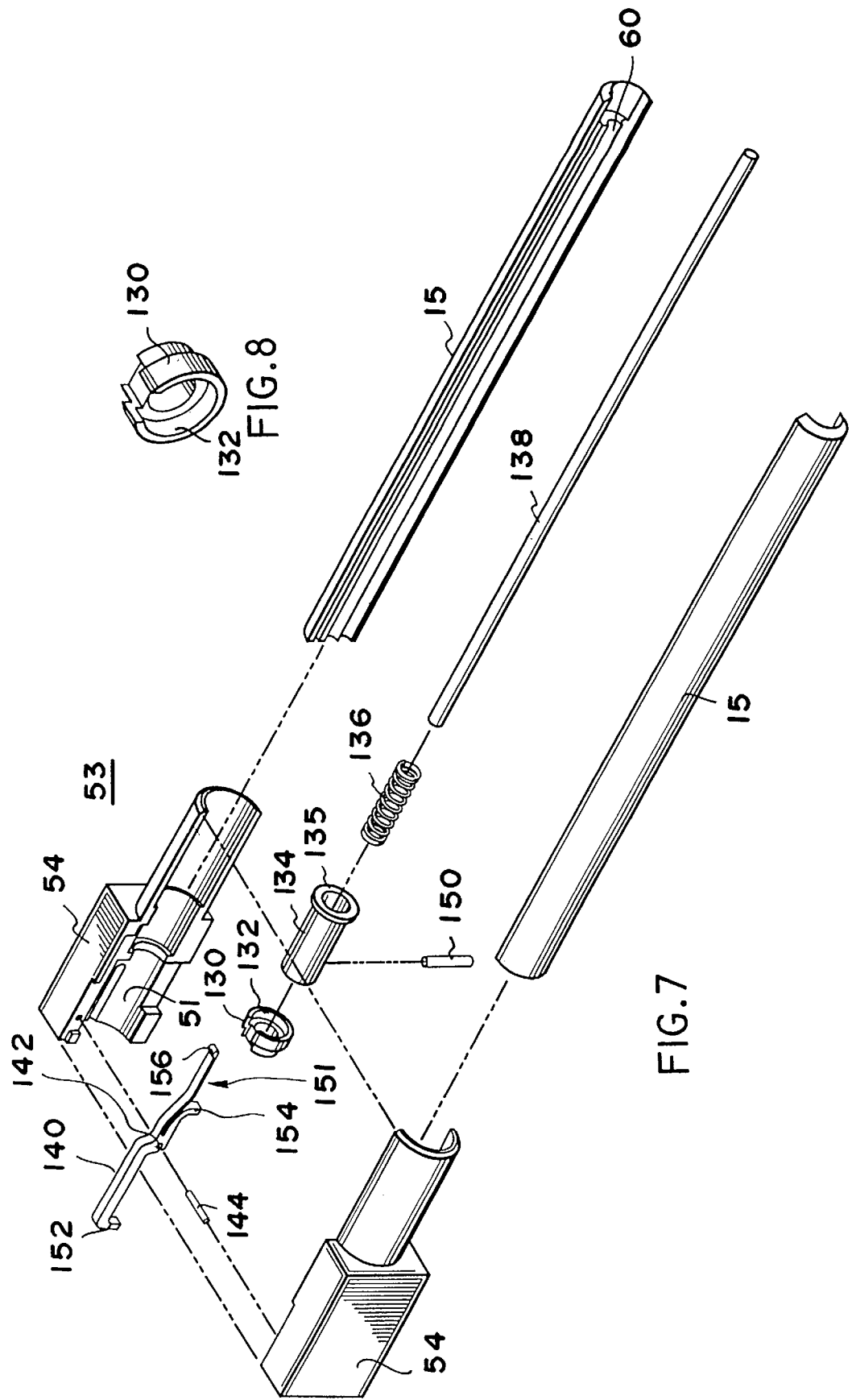

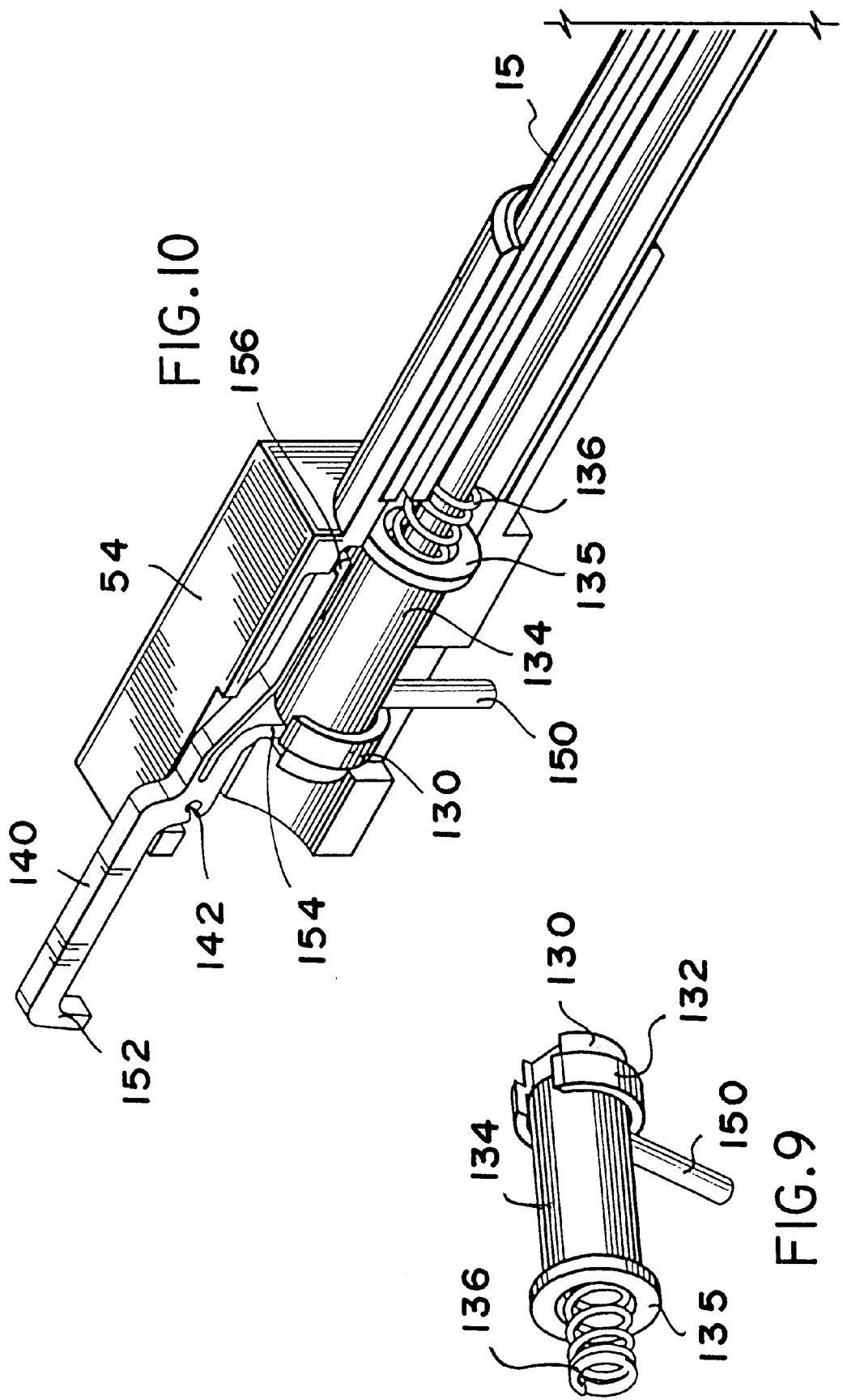

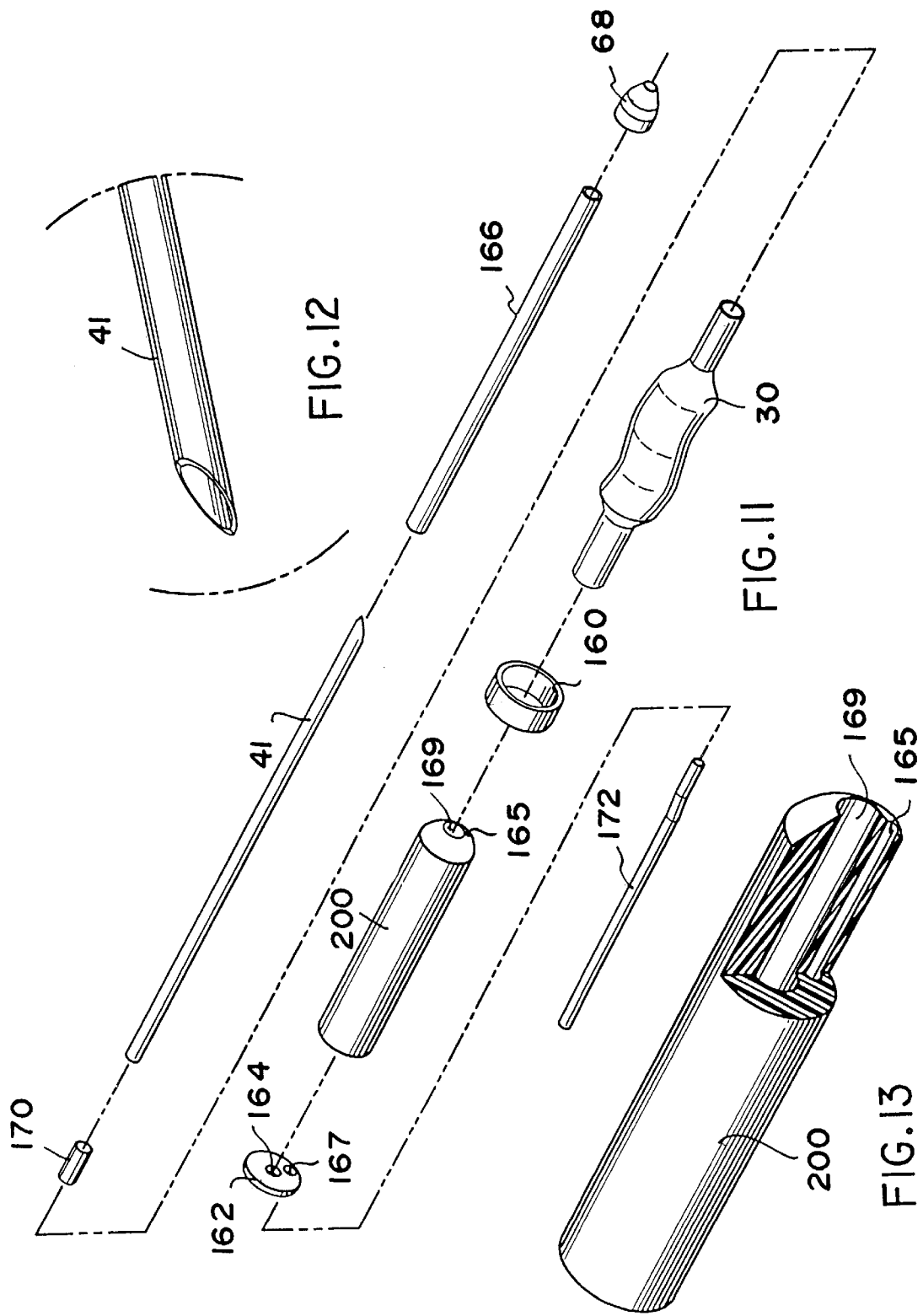

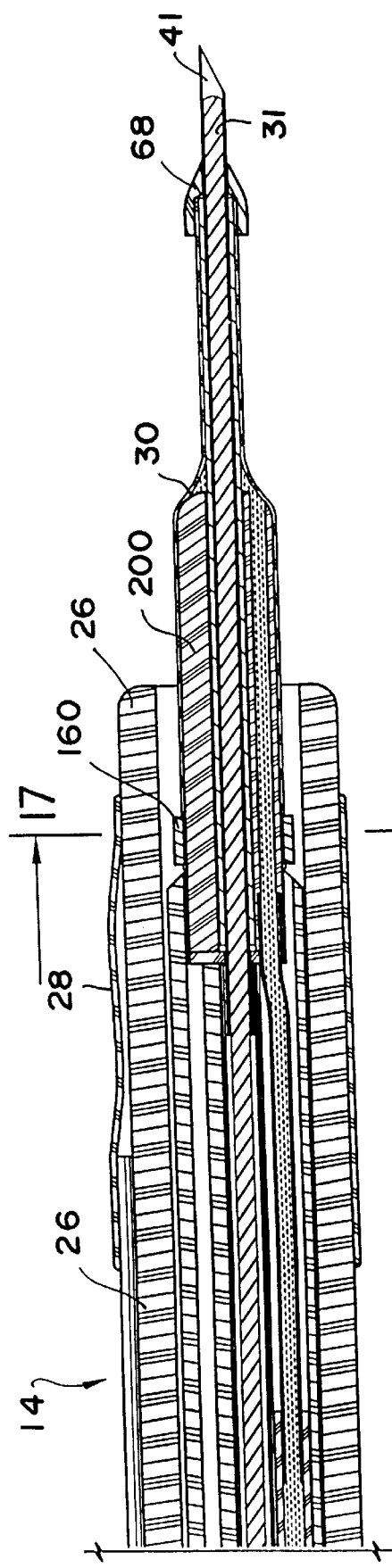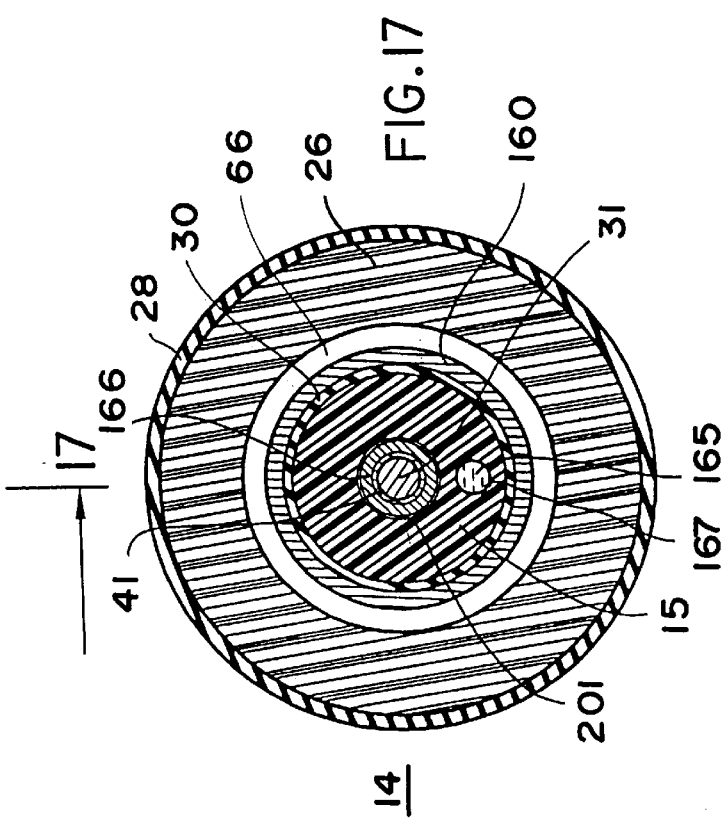

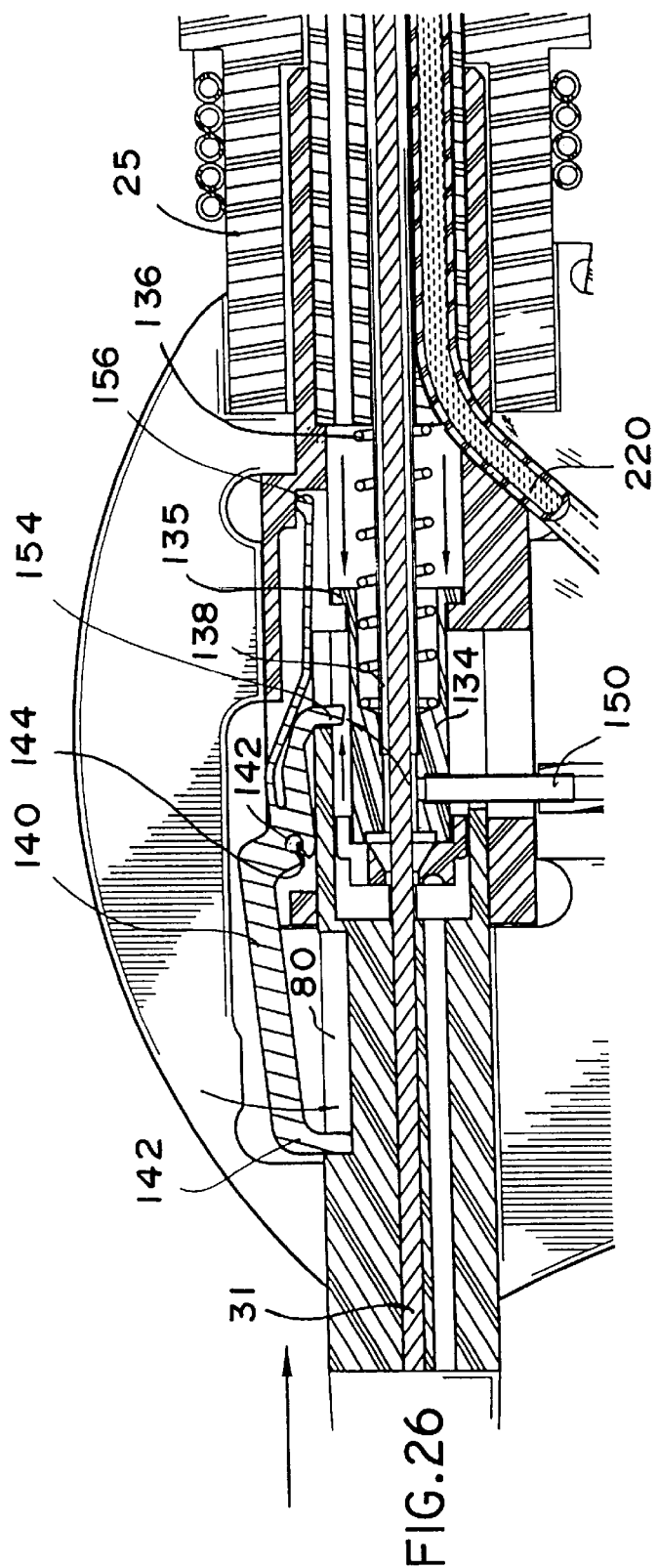
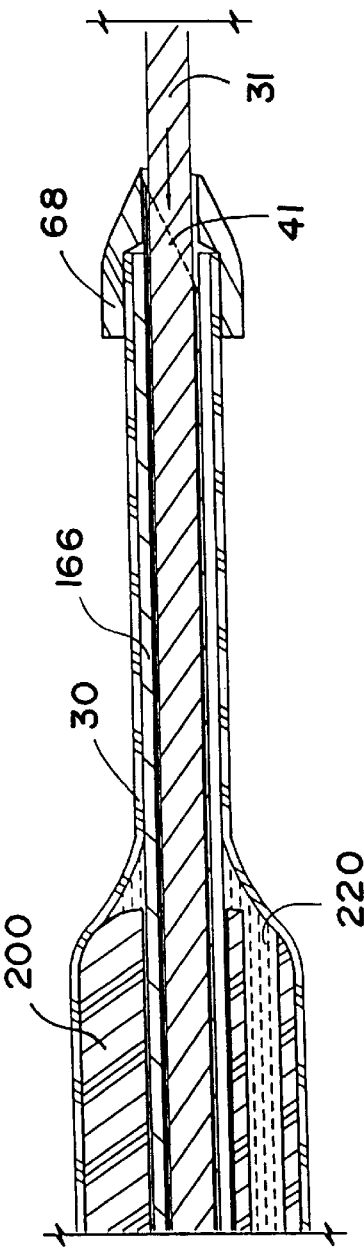
FIG. 26
FIG. 27

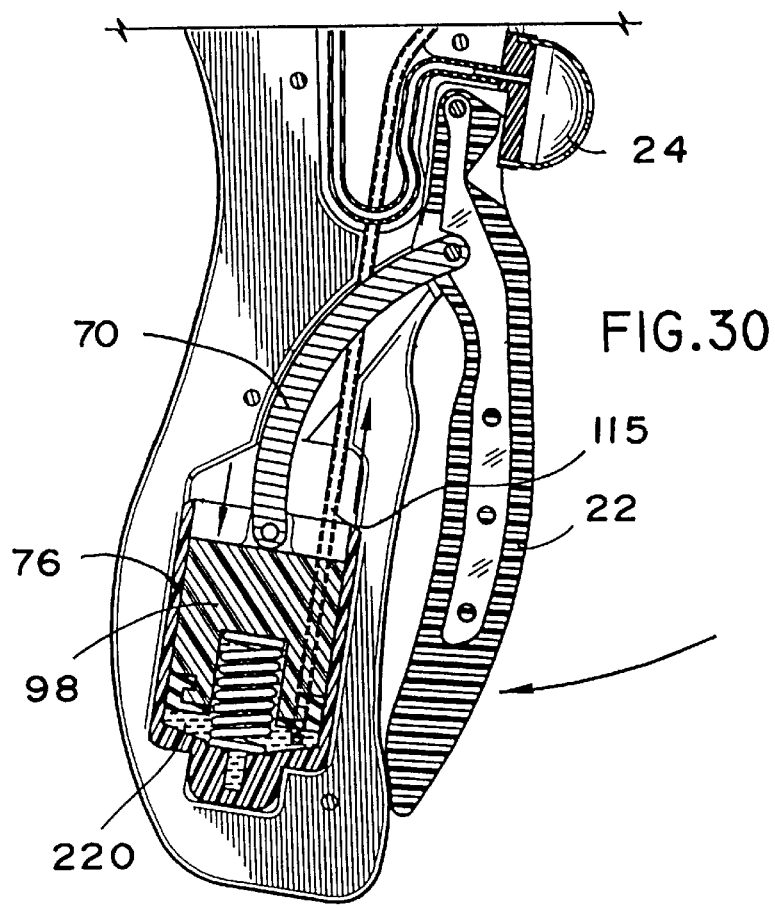
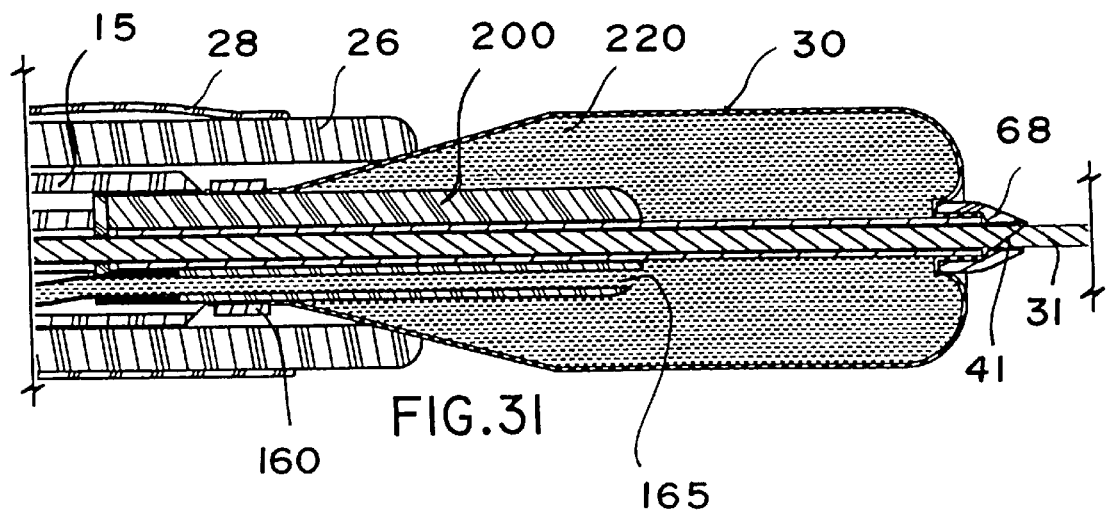

APPARATUS FOR EXPANDING BODY TISSUE

CROSS-REFERENCE OF RELATED APPLICATIONS

This application is a continuation-in-part of commonly owned and copending U.S. patent application Ser. No. 08/592,056 filed Jan. 26, 1996, now U.S. Pat. No. 5,690,669 and also claims benefit of priority from commonly owned and copending U.S. Provisional Patent Application Ser. No. 60/015,785, filed Apr. 17, 1996.

FIELD OF THE INVENTION

The present disclosure relates to an apparatus for expanding body tissue and, more particularly, to an apparatus incorporating an inflatable member which is selectively inflatable with a trigger mechanism. The present disclosure further relates to the surgical use of the apparatus in performing a tracheostomy.

BACKGROUND

Surgical instruments incorporating inflatable membranes or balloons, commonly referred to as balloon catheter instruments, have a wide variety of applications including use in, for example, angioplasty devices for clearing an occluded or blocked artery, urethral sphincters, tissue expanders or dilators, etc. One type of balloon catheter incorporates a plunger disposed within a syringe housing. The plunger is axially advanceable within the syringe housing in response to pressure directly applied to the rear end of the plunger to dispense the inflation fluid within the balloon. Another type of balloon catheter includes a plunger which is rotatably mounted within the syringe housing. The plunger distally translates in response to rotation thereof to dispense the inflation fluid into the balloon. Examples of conventional balloon catheters are described in U.S. Pat. Nos. 4,832,692; 5,084,060; 5,147,300; and 5,284,480. Such devices are typically operated by trained health care providers, such as physicians, physician's assistants, paramedics, nurses, etc., for therapeutic intervention. For the purpose of the present application, these people are collectively referred to as operators.

Although conventional balloon catheters such as those described above and disclosed in the aforementioned patents have proven to be generally effective in certain applications, these devices suffer from a number of disadvantages which detract from their usefulness. In particular, one disadvantage of conventional balloon catheters is that such devices require a two handed operation, i.e., one hand creates the force necessary to move the plunger within the syringe housing while the other hand is used to hold and stabilize the catheter. As a consequence, the operator is incapable of performing any other dexterous maneuver during the application of the catheter. Other disadvantages of conventional balloon catheters include the inability to incrementally and selectively control the amount of fluid pressure supplied to the inflatable member, the insufficiency in providing structure to rapidly inflate or deflate the inflatable member, and the relative complexity of the operating components.

A device operable with one hand permits the free hand to be used for other functions. For example, in a percutaneous tracheostomy procedure, a device requiring both hands would not allow an operator to use one hand continuously to stabilize and position the anterior neck and trachea to provide a stable insertion site.

U.S. Pat. No. 5,147,300 to Robinson et al. describes a balloon catheter instrument which attempts to address some of the aforementioned shortcomings of conventional instruments. The Robinson '300 instrument includes a housing, a syringe body and a handle. A threaded plunger is attached to the handle and advances within the syringe body in response to rotation of the handle. The instrument further includes a half nut mechanism which is selectively engageable with the threaded plunger. When the half nut mechanism is in engaged relation with the threaded plunger, the plunger is advanced by rotation of the handle. In the disengaged position of the half nut mechanism, the plunger may be advanced by depressing the handle without any rotational movement.

There are certain disadvantages inherent in the design of the Robinson '300 instrument. For example, similar to the afore-described balloon catheter devices, the Robinson '300 instrument requires a two handed operation; one hand to hold the instrument and the other hand to rotate the handle to advance the plunger. The half nut mechanism, although providing a means for rapidly inflating or deflating the balloon, is relatively complex thereby increasing cost of the instrument and decreasing the economic feasibility of disposing the instrument after a minimal number of uses, or even single use.

The present invention is especially useful for the percutaneous (i.e. through skin) placement of a tracheostomy tube, which is a plastic tubular elongated airway that facilitates respiratory exchange via a hole in front of the neck. Modern tracheostomy tubes typically incorporate an inflatable cuff at the end of the tube to provide support and protection.

A standard open surgical tracheostomy, also commonly referred to as tracheostomy, is a procedure to make a surgical opening through the superior aspect of the neck and into the trachea, usually between the first and second tracheal cartilages. Open tracheostomy is a time consuming, expensive and sometimes dangerous procedure usually performed in an operating room. It usually involves extensive tissue dissection and retraction, plus special lighting and equipment. Cricothyroidotomy is a high morbidity, emergency surgical procedure performed higher in the neck for the placement of a tracheostomy tube. Over 80,000 tracheostomies are performed each year in the United States. At the time of the tracheostomy procedure, most patients already have artificial airway tubes in place through the nose or mouth; less than 5% of all tracheostomies are emergency procedures.

Several percutaneous tracheostomy procedures have been developed to allow the procedure to be conducted at the patient's bedside. The most common approach uses a series of progressively larger diameter mechanical dilators passed over a guide wire. The implementation of the serial dilators requires use of both hands. Thus, the operator does not have a free hand, useful, for example, to stabilize the neck. Contemporary percutaneous progressive mechanical dilation techniques are slow, awkward and often dangerous.

Better percutaneous tracheostomy equipment and techniques are needed.

SUMMARY OF THE INVENTION

Accordingly, the present disclosure is directed to an improved apparatus which is useful in performing a wide variety of medical procedures such as percutaneous tracheostomy, angioplasty, tissue retraction, or tissue manipulation, etc. The apparatus can be operated and manipulated by a single hand, thus freeing the other hand to perform additional functions. The apparatus includes structure to permit rapid inflation or deflation of an inflatable member supported at the distal end of the instrument. In addition, the apparatus is simple in design and relatively inexpensive to manufacture, thereby rendering the apparatus disposable after a minimal number of uses or even a single use. The device also provides enhanced safety to patient and operator while being ergonomically pleasing.

Generally stated, the present disclosure is directed to a surgical apparatus for manipulating body tissue. The apparatus includes a handle member consisting of a frame, a self-contained fluid dispenser having a chamber with a supply of inflation fluid, a pump within the chamber for dispensing the inflation fluid, and a trigger operatively connected to the pump and moveable to cause corresponding movement of the pump and fluid. In addition, the apparatus comprises an aspirator that can be operated with a single digit of the same hand operating the device. The apparatus further includes a generally elongated member connected to the handle member and an inflatable dilator supported at the distal end portion of the elongated member in fluid communication with the fluid dispenser. The elongated member also includes a longitudinal passageway for permitting passage of a guide wire used in positioning the apparatus in the body tissue. The guide wire is attached to a fixture that is manipulated by a digit from the same hand such that the entire operation of the device, including needle retraction, can be accomplished using one hand.

In another embodiment, the present invention relates to an apparatus for performing a one handed percutaneous tracheostomy comprising a hollow needle, a bulb connected to the needle for aspirating air through an end of the needle, a flexible guide wire extending through the needle, and a fitting on one end of the guide wire for permitting the guide wire to be reciprocated with the same hand that holds the instrument, from a retracted position substantially within the needle, to an extended position in which a substantial length of the guide wire extends beyond an end of the needle. An expandable dilator is attached to the dilation tip for dilating a tracheal wall when the dilator is inflated, and a tracheostomy tube is detachably mounted with respect to the dilator for placement into a lumen of a trachea. In a particularly preferred embodiment the needle is retractable and the expandable dilator comprises an inflatable dilator.

In another embodiment, the invention relates to an apparatus for performing a one-handed tracheostomy, the improvement for locating the lumen of the trachea comprising a needle extending from the apparatus for insertion through a tracheal wall into the lumen of the trachea and a manually operable bulb, coupled to the needle for aspirating air through the needle for determining whether an end of the needle is located in the lumen of the trachea or in the tracheal wall. The bulb is positioned on the apparatus for operation by the one hand while gripping the apparatus. In a preferred embodiment, the needle is retractable and also comprises a resilient guide wire extending through the needle, a fitting preferably in the shape of a thumb ring on a proximal end of the guide wire for engagement with the one hand used to grip the apparatus, and a distal end of the guide wire extendable into the trachea for determining, by reciprocal movement of the guide wire, when the distal end of the wire is positioned in the lumen of the trachea for guiding a tracheostomy tube into the lumen of the trachea.

In a still further embodiment, the invention relates to an improved apparatus for performing a one-handed tracheostomy and guiding a tracheostomy tube into the lumen of the trachea, the apparatus comprising a resilient guide wire having a fitting on a proximal end for engagement with the one hand used to grip the apparatus and a distal end extendable into the trachea for determining, by reciprocal movement of the guide wire, when the distal end of the wire is positioned in the lumen of the trachea.

In another embodiment, the present invention relates to a method for performing a one-handed percutaneous tracheostomy comprising inserting a hollow needle through a tracheal wall with the one hand, deflating a bulb with the one hand to aspirate air through the needle to verify that the needle is within the lumen of a trachea, extending a guide wire from an end of the needle with the one hand, retracting the needle from the trachea while leaving the guide wire in place, extending an expandable dialator over the guide wire into the tracheal wall, expanding the dialator with the one hand to dilate the tracheal wall, and sliding a tracheostomy tube into the lumen of the trachea.

In another embodiment, the invention relates to a method for performing a percutaneous tracheostomy comprising inserting a hollow needle through a tracheal wall, aspirating air through the needle to verify that the needle is within the lumen of a trachea, extending a guide wire from an end of the needle, oscillating the guide wire to ensure that it is in the lumen of the trachea, retracting the needle from the trachea while leaving the guide wire in place, inserting an expandable dialator into the tracheal wall, expanding the dialator to dilate the tracheal wall, inserting a tracheostomy tube through the dilated tracheal wall into the lumen of the trachea, at least partially deflating the expandable dilator; and removing the dilator through the tracheostomy tube.

The present invention still further relates to a method for locating a distal end of a needle of a handheld instrument for performing a tracheostomy in an airway comprising compressing a resilient bulb on the instrument to aspirate air throuth the needle and observing the rate at which the bulb reexpands.

In a still further embodiment, the present invention relates to a surgical kit for manipulating body tissue comprising a tracheostomy tube and an apparatus comprising a hollow needle, a bulb connected to the needle for aspirating air through an end of the needle, a flexible guide wire extending through the needle, a fitting preferably in the shape of a thumb ring on one end of the guide wire for permitting the guide wire to be reciprocated with the same hand that holds the instrument, from a retracted position substantially within the needle, to an extended position in which a substantial length of the guide wire extends beyond an end of the needle, and an expandable dilator attached to the dilation tip for dilating a tracheal wall when the dilator is inflated. The kit may further comprise an antiseptic, sterile dressing, sterile gauze, at least one syringe, a scalpel and a needle.

BRIEF DESCRIPTION OF THE DRAWINGS

Preferred embodiments of the disclosure are described hereinbelow with reference to the drawings wherein:

FIG. 2 is a perspective view of the apparatus illustrating the safety cover unit and the elongated member with the expandable dilator being an inflatable dilator;

FIG. 3 is a perspective view of the apparatus with the safety cover positioned on the elongated member;

FIG. 4 is an exploded view of the apparatus of FIG. 1;

FIG. 5 is an enlarged view of the thumb ring fitting;

FIG. 6 is an exploded view of the handle assembly;

FIG. 7 is an exploded view of the needle retraction system;

FIG. 8 is a perspective view of the reset cap;

FIG. 9 is a perspective view of assembled sub parts of the needle retraction system;

FIG. 10 is a perspective exposed view of the needle retraction system;

FIG. 11 is an exploded view of a portion of the inflation system;

FIG. 12 is an enlarged perspective side view of the needle;

FIG. 13 is a perspective partial cross-sectional view of the elongated member illustrating the passageway contained therein;

FIG. 16 is an enlarged side elevation cross-sectional view of the distal portion of the assembly;

FIG. 17 is a cross-sectional view of FIG. 16 taken along the line 17—17;

FIG. 26 is a further illustration of the operation of the retractable needle system;

FIG. 27 illustrates the retraction of the retractable needle into the distal portion of the elongated member;

FIG. 30 shows a cross-sectional side view of the handle assembly during inflation;

FIG. 31 shows a cross-sectional side view of the inflatable distal end of the device;

DETAILED DESCRIPTION OF THE INVENTION

Figure 1:
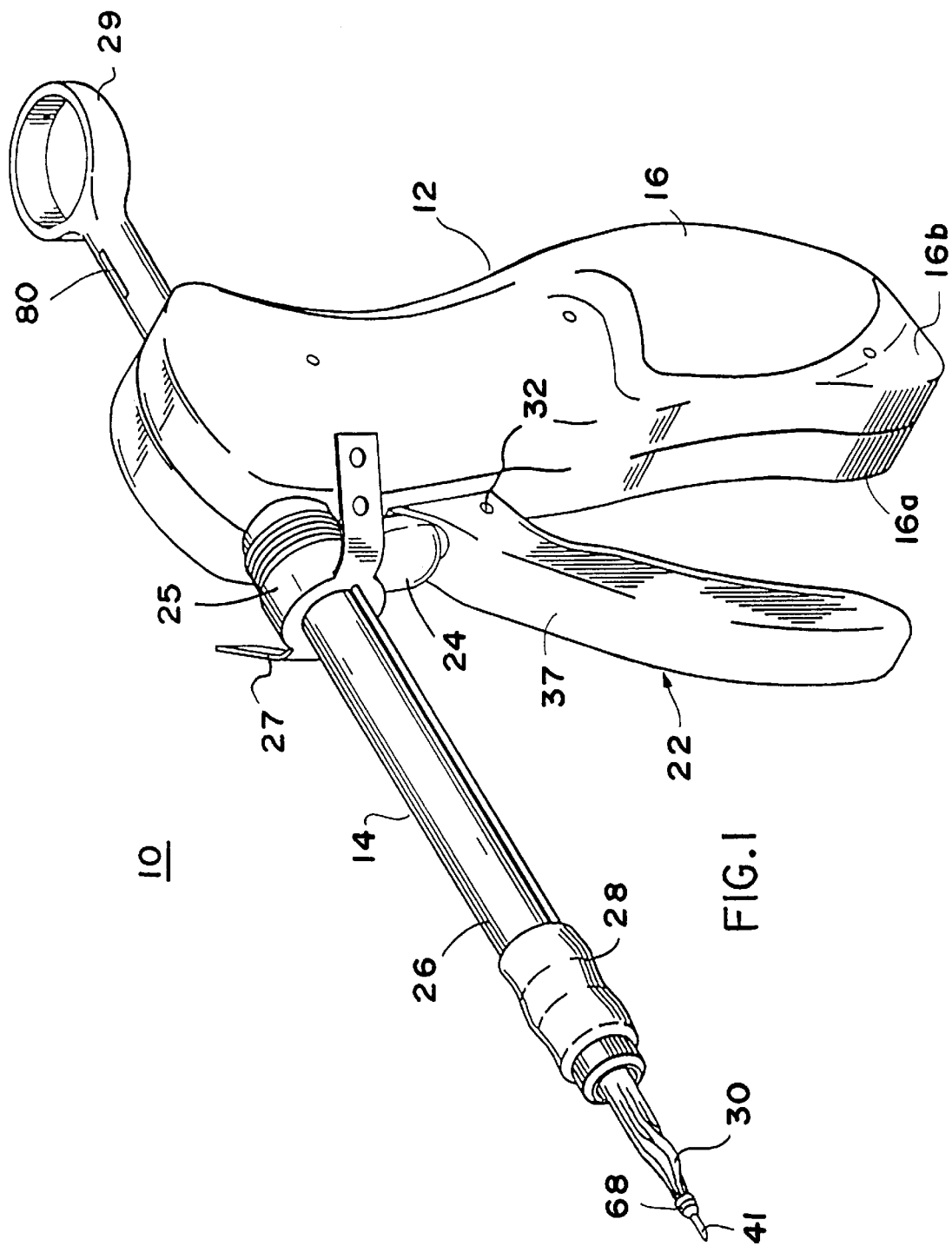
FIG. 1 is a perspective view of the apparatus in accordance with the principals of the present disclosure.

The present invention is contemplated for use in medical procedures where manipulation, retraction and/or dilation of a body structure is required. While the apparatus is particularly useful in performing a tracheostomy and will be described in connection with performing this procedure, it is to be appreciated that the apparatus has application to other medical procedures as well. For example, the apparatus may be effectively used in enlarging or clearing an obstruction from vessels such as the coronary artery, fallopian tubes, urethral passages, etc. The present invention may also be useful when the elongated member loaded with a tube is initially passed through a natural orifice and then into a stenotic (i.e. narrowing) or obstructive lesion. For example, obstructive rectal or esophageal lesions may be widened and intubated through the anus or mouth, respectively.

Referring now to FIGS. 1–6, there is illustrated a preferred embodiment of the apparatus constructed in accordance with the principles of the present disclosure. Apparatus 10 includes handle unit 12 and elongated member 14 extending distally from the handle unit 12 and covered by tracheostomy tube 26 having flange strap 27. Handle unit 12 includes a frame 16 comprising two half sections 16a and 16b. In a preferred mounting method shown in FIG. 4, a plurality of mounting pins 18 are received within respective mounting apertures 20 defined in half sections 16a to assist in mounting the half sections 16a, 16b. Mounting pins 18 may be secured within mounting apertures 20 with cements, adhesives, or the like, or may be threaded, etc. Other means for affixing half sections 16a, 16b to each other may be readily determined by one skilled in the art such as with the use of adhesives, screws or other conventional fastening means.

As shown in FIG. 1, handle unit 12 further includes trigger 22, aspiration bulb 24, tracheostomy tube 26, inflatable tube segment or cuff 28 and inflatable dilator 30. Trigger 22 is pivotally mounted to frame 16 about pivot pin 32. Pivot pin 32 is preferably contiguously formed with trigger 22 as shown in FIG. 6 and is received within trigger mounting aperture 34 formed in each half section 16a, 16b to effectuate the mounting. Trigger 22 includes grip portion 37 which may be a contoured gripping surface strategically dimensioned to be grasped by the user. In a preferred embodiment, sections of the handle are also contoured to facilitate proper gripping by the user. The trigger 22 follows an arcuate path and is received within correspondingly dimensioned arcuate guide channels 40 (FIG. 6) formed in each half section 16a, 16b.

FIGS. 2–3 depict another perspective view of the apparatus with a protective cap 50 in place. The cap may be held in place by frictional forces, or by snapping into place by positioning complementary surfaces on the inside of the cap and the tube 26 exterior, or by any sterilizable fastening means.

FIG. 4 is an exploded perspective view of the apparatus 10 showing half sections 16a, 16b. A fitting, most preferably shaped into a thumb ring 29 having keyway 80 and flexible guide wire 31 fits into frame 16. Tube 131 fits over wire 31 to insure that an hermetic seal is maintained as the guide wire is oscillated. Half section 16b is shown containing trigger 22, aspiration bulb 24, and pivot arm 70 connected to tabs 73, 74 of piston head 98 disposed into pump housing 76. Needle 41 is shown extending from dilator tip 68. Inflatable dilator 30 is clamped at one end by dilator tip 68 and at a second end by crimp ring mounting mechanism 60 onto balloon mount 200. Sleeve 166 is shown extending from mount 200.

As shown in FIG. 5, thumb ring fitting 29 has keyway 80 cut into its cylindrical segment. Notch 84 is present in the open end of the cylindrical segment. Channels 88, 90 are bored through the solid segment of the thumb ring.

FIG. 6 is an exploded perspective view of the pump assembly 72, comprising housing 76 which rests in the housing cavity 92 in handle half section 16b. Spring 94 is positioned within gasket 96 which seats piston head 98 in housing 76. Pin 100 connects piston head 98 to piston arm 70 through tabs 73, 74. Trigger 22 is secured to half 16b with pivot pin 32 which fits into trigger mounting aperture 34. Pin 102 fits through aperture 104 in trigger and piston arm aperture 106. Aspiration bulb 24 is secured against plate 108 via clamp 110 which is secured against raised portion 112 of plate 108. Throughway 114 in plate 108 provides access into and out of plate 108. Bulb 24 rests in trigger recess 116. Tube 118 connects to stem 117 and passes into a channel within the elongated member 14 and can direct air and receive fluid through needle 41. Retention clip 120 seats thumb ring 29 into chamber 42.

FIG. 7 is an exploded perspective view of the needle retraction mechanism 53. Cylindrical reset cap 130 is housed within retraction housing 54. Reset cap 130 has a flange 132 which seats needle bushing 134. Spring 136 fits into bushing 134. Needle driver 138 abuts spring 136 in bushing 134. Inner tube 15 of the elongated member segment 14 of the apparatus 10 houses the needle driver 138. Inner tube 15 has longitudinal bore 60 dimensioned to receive needle driver 138. Needle latch 140 has a pivot aperture 142 through which pivot pin 144 fits. Retraction housing 54 fits into an appropriately dimensioned cavity in the apparatus housing 16. Aspirator fitting 150 is received into an opening (not shown) in bushing 134.

FIGS. 9 and 10 show the assembled needle retraction assembly. In FIG. 9, the retraction bushing 134 is shown in place abutting flange 132 of reset cap 130, with spring 136 extending from the bushing. FIG. 10 shows an exposed view of the needle retraction assembly, in place in the cavity 51 (FIG. 7) of retraction housing 54. The needle retraction system includes a needle latch 140; a needle bushing 134; a reset cap 130; a spring 136; a needle driver 138; and a needle 41, wherein the needle latch cooperates with corresponding keyway 80 in the thumb ring fitting 29.

The needle includes a leading hooked limiter end 152 and a tail end 151. The proximate end of the needle 41 is cooperatively engaged with the needle driver 138 via spacer 170. The proximate end of the needle driver 138 is fixedly attached to the needle bushing 134. The needle 41, needle driver 138, needle bushing 134 and reset cap 130 define a passageway through which the guide wire 30 is slideably moveable.

The needle bushing 134 is generally a cylindrical member having an aperture therethrough, with a larger diameter opening at one end to define a flange 135. The flange cooperatively engages one end of the spring 136. The remaining end of the spring engages the elongated member 14. The remaining end of the needle bushing is fixedly attached to a reset cap 130. The reset cap 130 helps center the needle bushing.

The needle latch 140 includes a trigger end 154 and a limiter end 152. The needle latch is pivotally mounted to the retraction housing 54 intermediate the trigger end and the limiter end. The trigger end includes a generally L-shaped member having an angled camping surface, wherein the bottom of the L portion selectively contacts the needle bushing flange and the camming surface selectively contact the thumb ring.

In the needle extended position, the needle bushing, and hence driver and needle are disposed toward the distal end of the elongate member. This compresses the spring, and the needle bushing cooperatively engages the trigger end of the needle latch.

FIG. 11 is an exploded view of the needle assembly within the distal end of the apparatus 10. Balloon mount 200 has central aperture or channel 169 passing longitudinally through its length. Sleeve 166 abuts dilator tip 68 at one end, and spacer 170 at the other end. Needle 41 is dimensioned to fit and move freely within sleeve 166. Tube 172 extends through aperture 167 in washer 162 and abuts aperture 165 in balloon mount 200. Washer 162 seals a first end of balloon mount 200. The second end of mount 200 is secured to the inflatable dilator 30, by crimp ring 160.

FIG. 12 is an enlarged view of the terminal end of needle 41. FIG. 13 shows a partially exposed view of balloon mount 200 showing central aperture 169 and inflation fluid channel 165.

Figure 14:
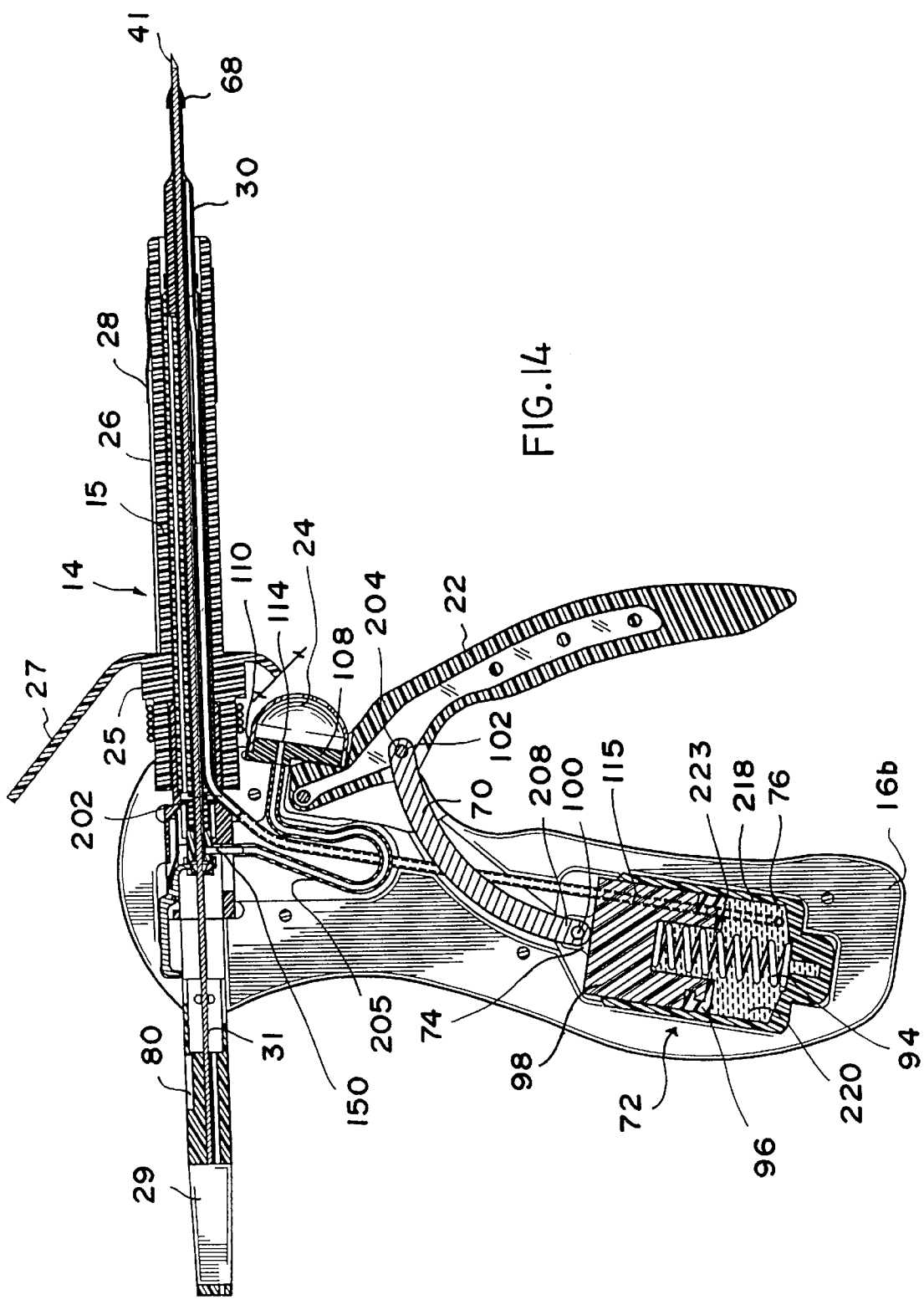
FIG. 14 is a side elevation cross sectional view of the apparatus of FIG. 1.
Figure 15:
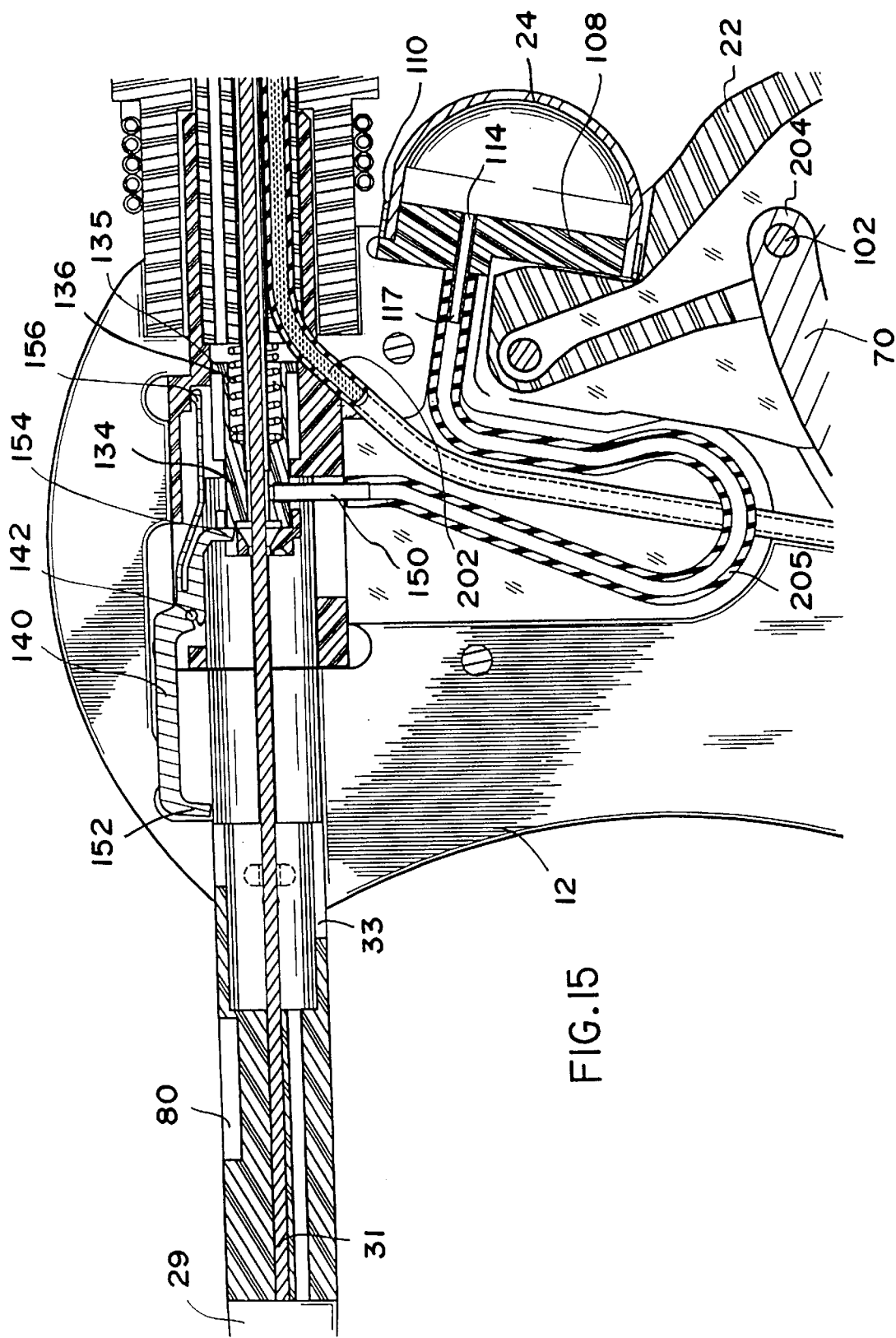
FIG. 15 is an enlarged side elevational cross-sectional view of a portion of the assembly of FIG. 14.

FIGS. 14 and 15 are cross-sectional side views of apparatus 10. Thumb ring 29 with attached guide wire 31 engages collar. Upon needle retraction, limiter end 152 engages keyway 80 to allow for limited oscillation of the guide wire and prohibits the flexible guide wire from retracting fully into the dilator tip. Guide wire 31 extends through length of needle 41. A seal (not shown) between the guide wire 31 and the collar maintains the hermetic communication between the aspiration bulb tip of the instrument. Aspirator bulb 24 has passageway 114 extending through plate channel 114 through stem 117 to tube 205 which connects to aspirator fitting 150. Trigger 22 connects to pivot arm 70 at first end 204 of pivot arm 70 by connector 102. Second end 208 of pivot arm 70 is connected to pump 210 by connector 212 at tabs 73, 74. Pump assembly 72 comprises piston 98 and spring 94. Fluid 220 rests in chamber 76. Seal 223 is secured to the bottom of piston 98 to interface with the fluid 220 and gasket 96 to effect a pressure tight seal. Tube 115 is submerged in fluid 220 and extends through apparatus body and connects to inflation channel 202, which extends through the inner tube 15 of elongated member 14 and terminates at the inflatable dilator 30.

FIG. 16 shows an enlarged cross-sectional side view of the terminal end of the needle assembly within elongated member 14 covered by tracheostomy tube 26 with inflatable cuff 28. Inflatable dilator 30 is shown in its deflated state. Channel 202 is shown filled with fluid 220 pumped from reservoir 218. Inflatable dilator 30 is attached to balloon mount 200 by crimp ring 160. Dilator tip 68 is fixably attached to the terminal end of sleeve 166. FIG. 17 shows a cross-section of elongated member 14 within tube 26 viewed along line 17—17 shown in FIG. 16. From the outermost radius inward is shown the inflatable cuff 28, the trachea tube 26, annular space 66, crimp ring 160, inflatable dilator 30, balloon mount 200, cavity 201, sleeve 166, needle 41 and guide wire 31.

Figure 18:
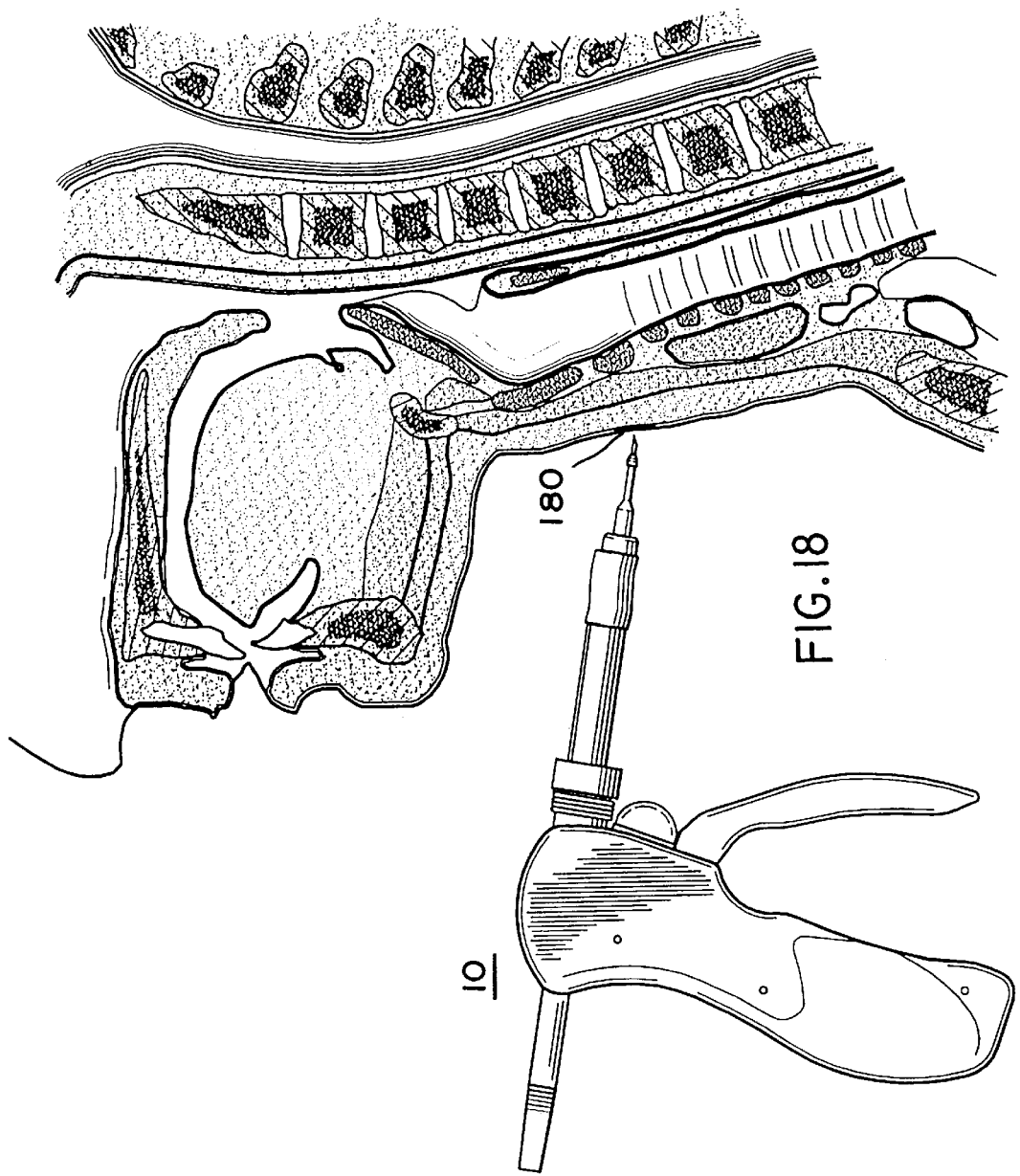
FIG. 18 is a view illustrating a preferred method for performing a tracheostomy with the apparatus of FIG. 1.
Figure 19:
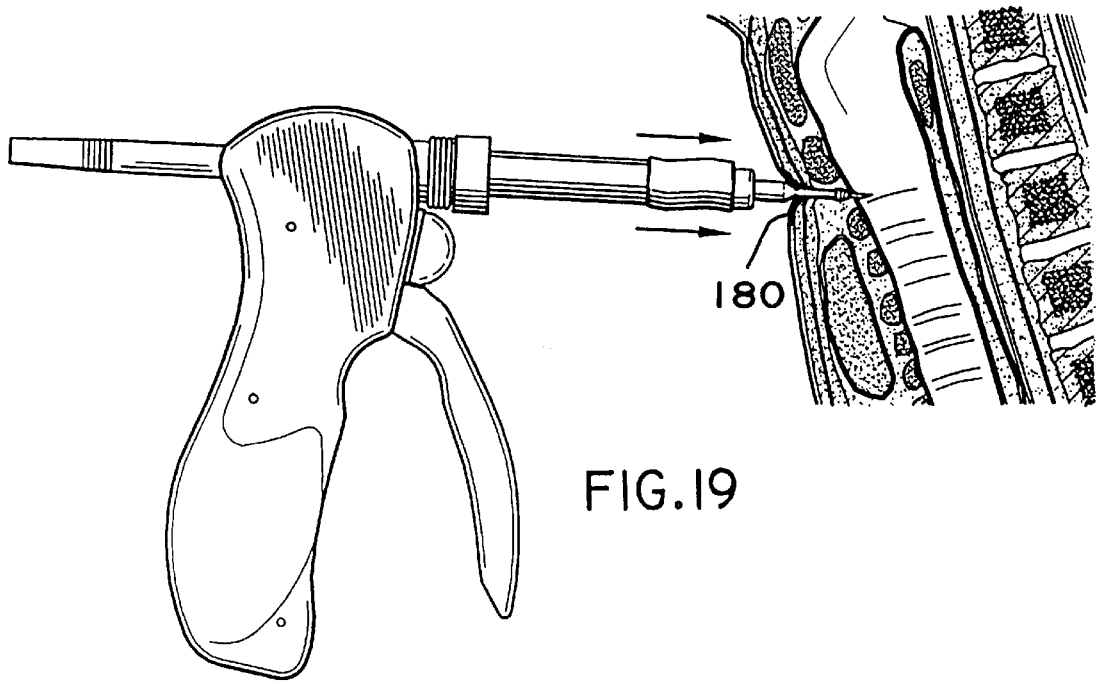
FIG. 19 is a view illustrating the insertion of the surgical device into the trachea.
Figure 20:
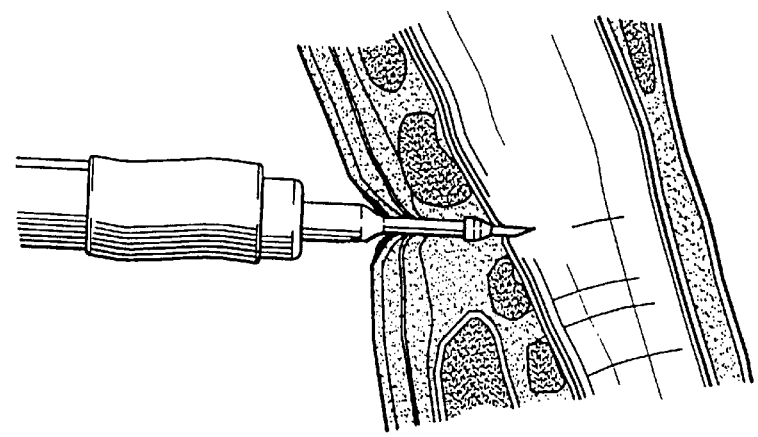
FIG. 20 is an enlarged illustration of a portion of FIG. 19.
Figure 21:
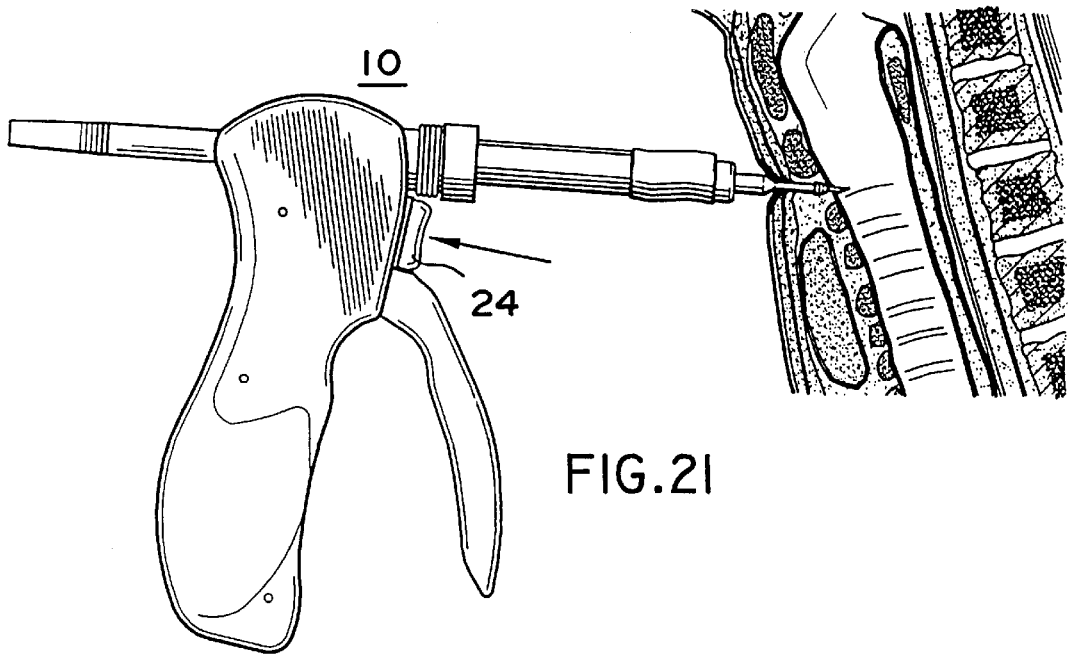
FIG. 21 is an illustration of the use of the aspiration chamber.

FIG. 18 shows the apparatus 10 positioned to enter a human neck through a vertical or horizontal skin incision. FIGS. 19 and 20 show the needle assembly proceeding through the incision penetrating the neck and into the tracheal lumen. This part of the human airway is a tubular structure connecting the mouth and nose with the lungs. The trachea contains horizontally oriented bands of cartilage to maintain its structure. For this procedure, the preferred location for needle penetration is typically between the first and second tracheal cartilages. At this point, as shown in FIG. 21, the aspirator bulb 24 is depressed. If the bulb reinflates rapidly it indicates that the needle tip is in communication with free air in the tracheal lumen, or air passageway. Thus free air flow indicates that the tip of the needle has pierced the tracheal wall.

Figure 22:
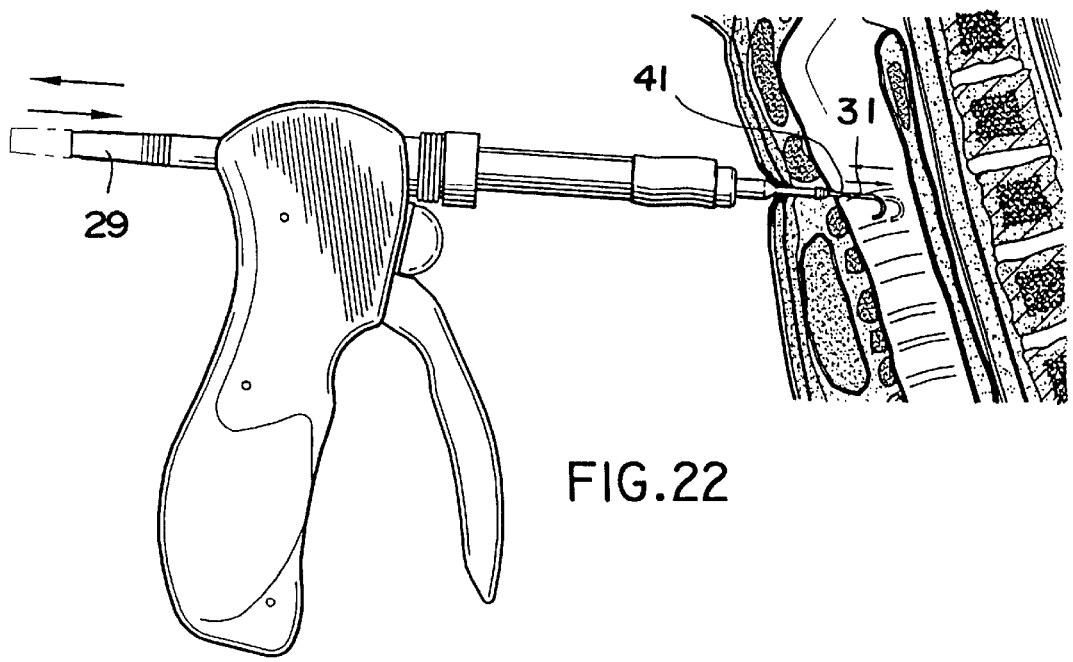
FIG. 22 is a view of the operation of the guide wire.
Figure 23:
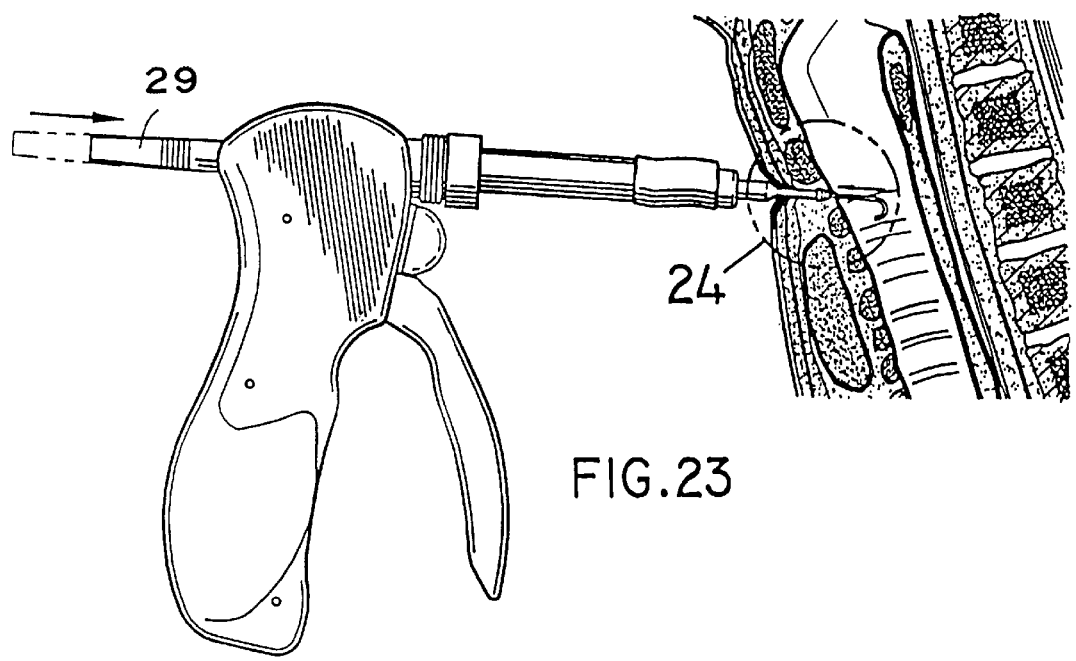
FIG. 23 is a view similar to FIG. 22 illustrating the operation of the needle retraction system.
Figure 24:
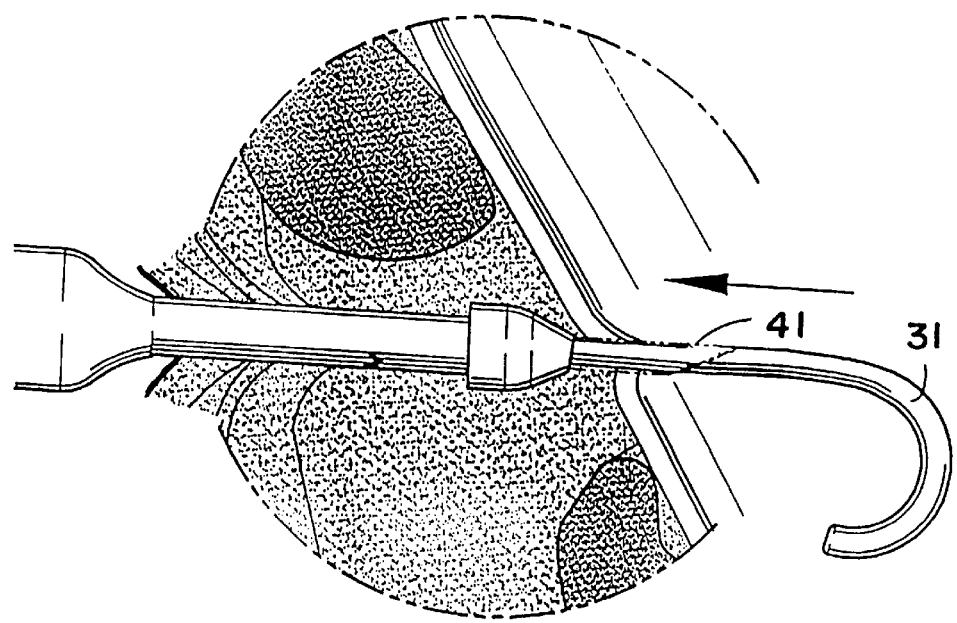
FIG. 24 is a enlarged view of FIG. 23 to illustrate the retraction of the retractable needle.

As shown in FIGS. 22 and 23, as the thumb ring fitting 29 is oscillated, guide wire 31 is then oscillated, alternately being extended into and withdrawn from the tracheal lumen. The preferred wire 31 has a curved distal end. Such oscillation of the guide wire into the tracheal lumen assures the operator that the apparatus tip is properly positioned in the tracheal lumen, an open air passageway. If the guide wire does not freely advance, it may indicate the tip of the instrument is still in solid tissue, not open lumen. Advancing such guide wire in solid tissue often causes it to kink and bind when guide wire retraction is attempted. In the enlarged view as shown in FIG. 24, the thumb ring fitting is fully brought forward into the device, causing the sharp cutting edge of the needle tip to retract to a point inside of the elongated member leaving only the atraumatic guide wire to guide the dilating tip into the tracheal lumen.

Figure 25:
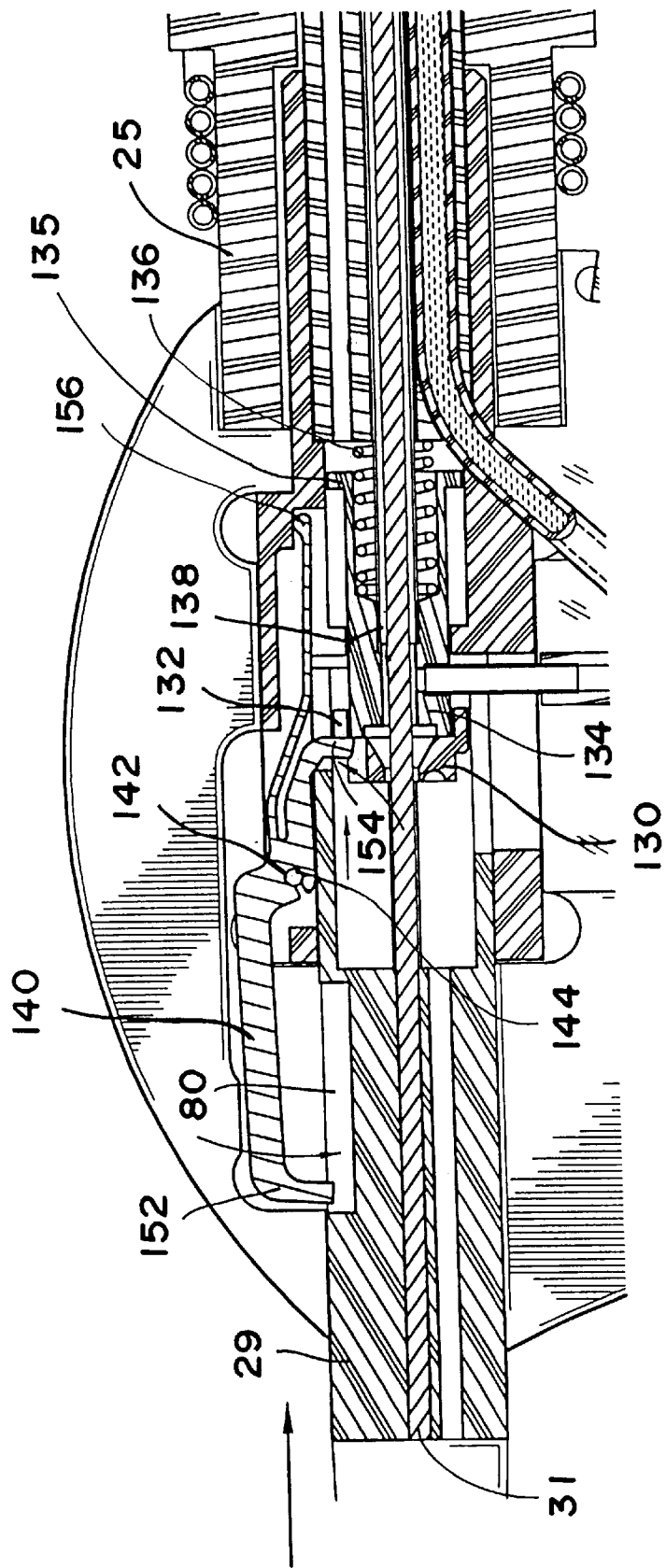
FIG. 25 is a enlarged cross-sectional view of the needle retraction system.

FIGS. 25 and 26 show a cross-sectional side view of the needle retraction assembly within the apparatus 10. The thumb ring 29 fitting has attached thereto one end of the guide wire 31. Thumb ring further has a keyway 80. Needle latch 140 is mounted about a pivot pin 144. Latch 140 comprises a hooked limiter end 152, a trigger end 154, and a tension bar 156. Reset cap 130 has flange 132 supporting trigger end 154. The distal end of needle 41 abuts needle bushing 134 having flange 135. Spring 136 is held in a compressed state adjacent the bushing 134 and the needle driver 138. FIG. 25 shows the thumb ring fitting 29 pushed into the apparatus 10 such that the needle latch can depress into the keyway 80. FIG. 26 shows the limiter end 152 of the latch 140, pivoting downward into the keyway 80, thus raising the trigger end 154 and allowing the spring 136 to exert force on the moveable needle bushing 134, thus retracting the needle driver 138 and the needle 41 into the balloon mount 200 and within the dilator tip 68.

FIG. 27 shows an enlarged, cross-sectional view of the needle moved to its retracted position wherein needle 41 does not extend past dilator tip 68.

Figure 28:
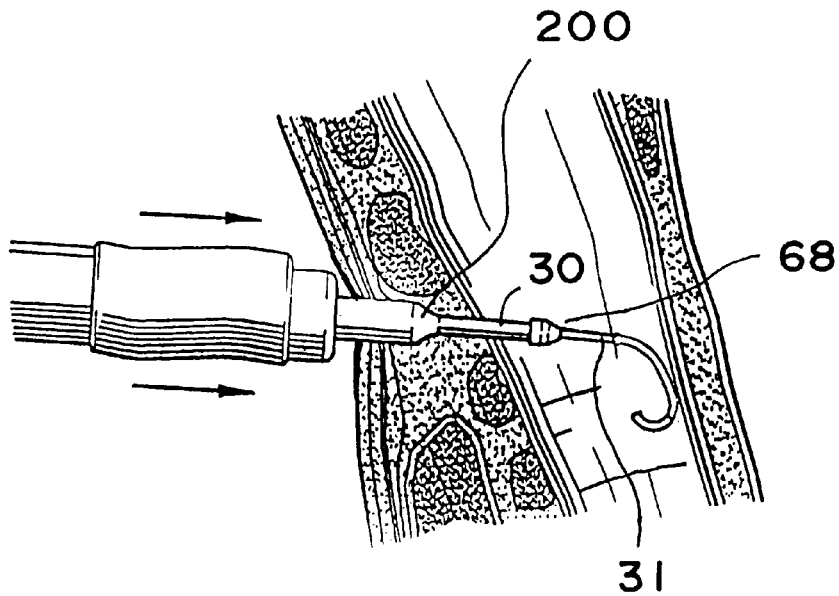
FIG. 28 illustrates the insertion of the dilator tip into the trachea.
Figure 29:
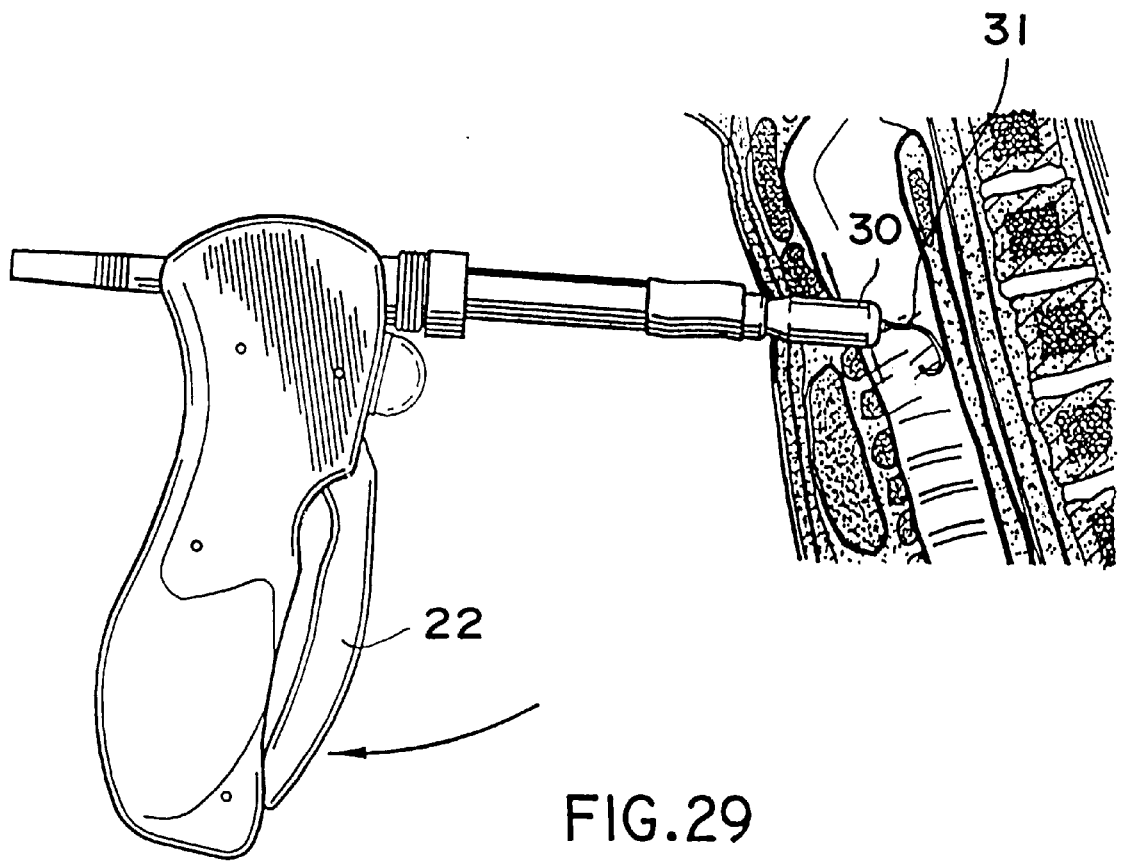
FIG. 29 illustrates the inflation of the inflatable dilator in a wall of the trachea.

FIGS. 28 and 29 show a particularly preferred embodiment wherein the apparatus is inserted into position to continue a tracheal intubation procedure after the needle has been retracted with the guide wire left passing through the hollow length of the needle. Using the guide wire to establish the track into the tracheal lumen, inward force causes the dilator tip to pass through the tracheal wall into the lumen. Next, the smaller diameter sleeve 166 covered with the tightly folded down inflatable dilator 30 slides through the hole in the tracheal wall and into the lumen. The balloon mount 200 stops outside of the hole in the tracheal wall since the outer diameter of the balloon mount is larger than the diameter of the inflatable dilator 30 in its uninflated state. At this point, the operator confirms that the apparatus dilator tip is inside the lumen, while the balloon mount is outside the trachea. Thus, the body of the balloon traverses the wall of the trachea. Trigger 22 is compressed against the apparatus body forcing the piston 98 to be forced into the pump housing. Inflatable dilator 30 is shown in its original (FIG. 28) and inflated (FIG. 29) states. FIG. 30 is an enlarged cross-sectional view of the pump mechanism used to inflate the dilator 30. FIG. 31 shows an enlarged cross-sectional view of the dilator 30 in an inflated state, clearly showing the fluid stream and channel 165 which extends through inner tube 15.

Figure 32:
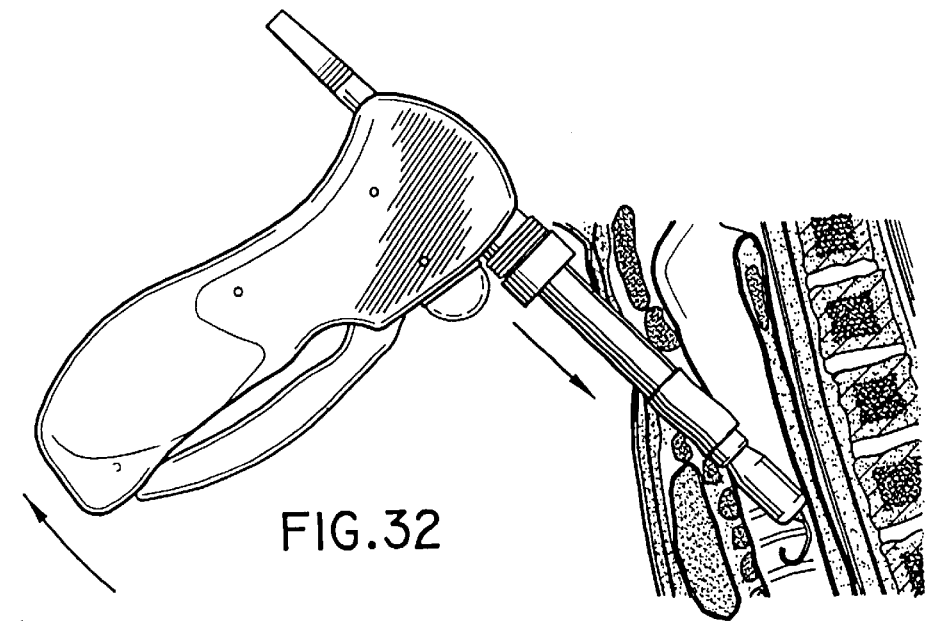
FIG. 32 illustrates the further insertion of the surgical device into the trachea.
Figure 33:
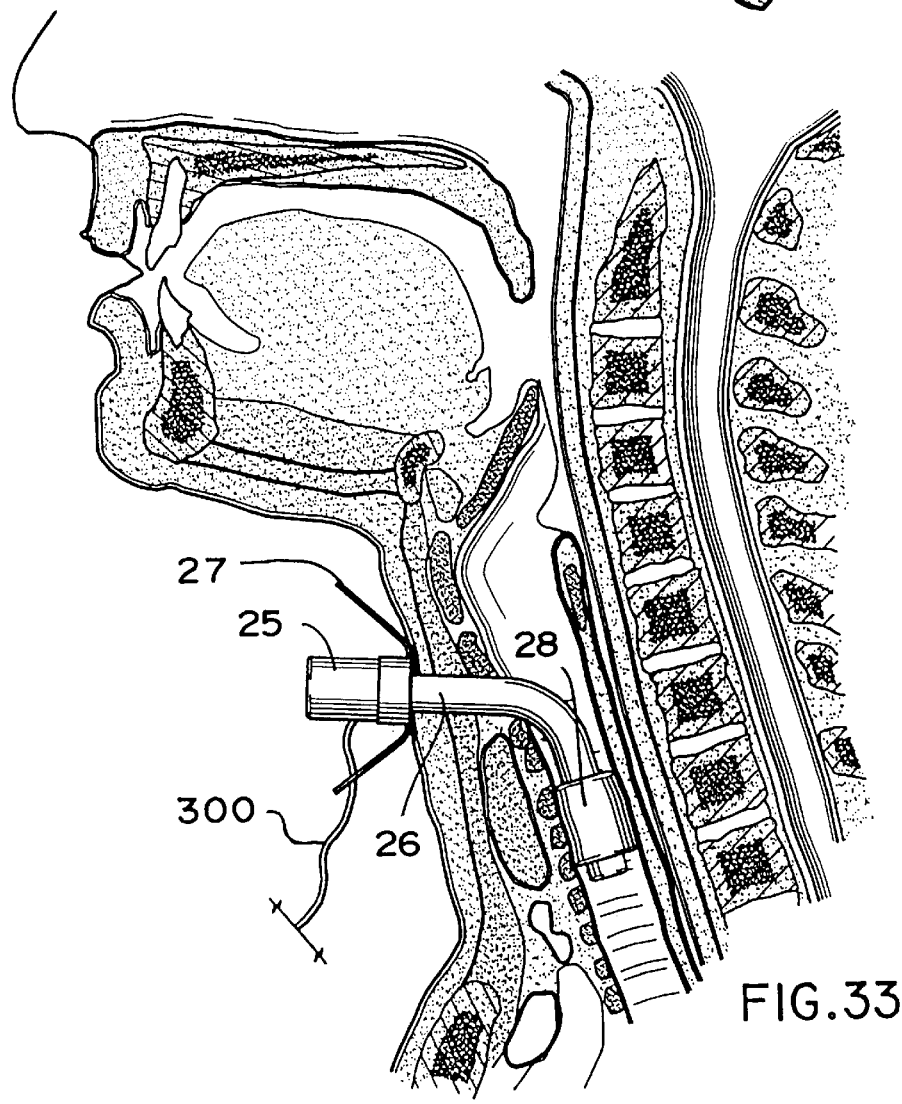
FIG. 33 illustrates the position of the tracheostomy tube within the trachea with the tube cuff inflated.

In FIG. 32, apparatus 10 is inserted angularly into the trachea. After this, expandable dilator is deflated partially or completely and apparatus 10 is withdrawn from disengageable tube 26 which is held in place in the trachea. As shown in FIG. 33, the cuff 28 is inflated via airflow intake tube 300. Inflation of cuff 28 holds tube 26 in place.

Figure 34:
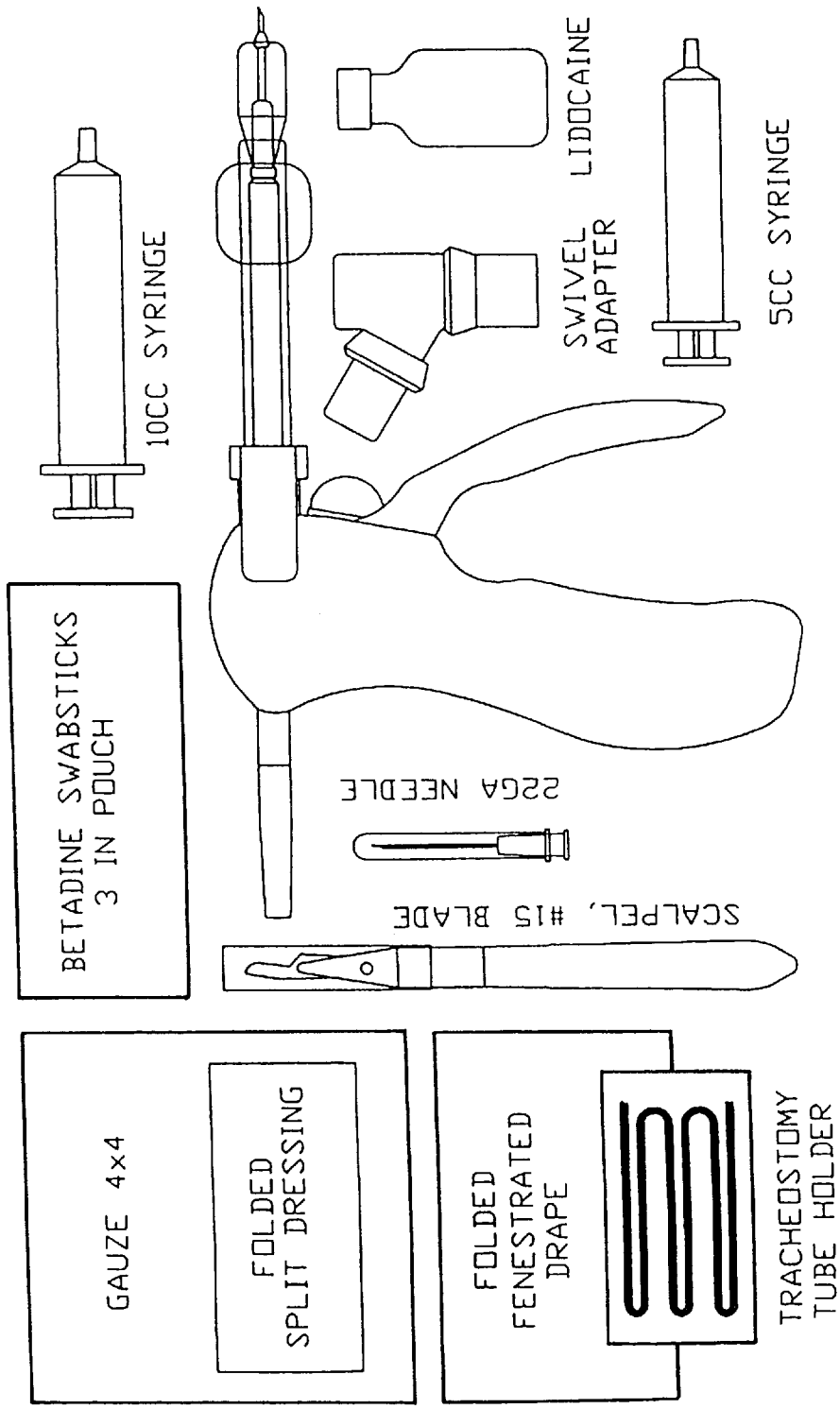
FIG. 34 is a diagrammatic view of a kit for performing a percutaneous tracheostomy in accordance with the invention.

FIG. 34 depicts a kit, preferably for performing tracheostomies, comprising the apparatus 10 of the present invention, arranged with the accompanying articles required to perform various methods of the present invention. The kit comprises the apparatus of the present invention, a container of an amount of aneshthetic, preferably lidocaine, a tracheostomy tube of a predetermined size, a 10 cc syringe, a 5 cc syringe, a tracheostomy tube swivel adapter, a needle of a predetermined gauge, preferably a 22 gauge, a scalpel, antiseptic preferably betadine solution on stick or swap supports, multiple gauze dressings and a folded fenestrated drape and a tracheostomy tube holder.

The operation of apparatus 10 will now be discussed. Referring initially to FIGS. 4 and 6, when it is desired to manipulate or dilate tissue during a surgical procedure, the surgeon grasps handle unit 12 and positions the apparatus 10 adjacent the tissue to be expanded. In accordance with a preferred method of using apparatus 10, a skin incision is made in the neck of a patient. The needle of the apparatus is then inserted through the incision to pierce underlying body tissue, such as fat and fascia, and finally the tracheal wall. The aspirator bulb is then depressed. The operator detects proper placement of the apparatus by sensing the resistance to the applied pressure from the depressed aspiration bulb. An easily depressed aspiration bulb followed by easy reinflation indicates that the needle has pierced the tracheal wall and is positioned in the tracheal lumen. Pressurized air is communicated to the trachea through aspiration passageway tube 205. The proper placement of the needle and the instant device into the trachea is confirmed upon rapid reinflation of the aspiration bulb. If the bulb does not reinflate readily, the operator may reposition the needle or remove the entire apparatus and begin again.

Subsequent to the confirmation of the passage of the needle 41 through the tracheal wall, the guide wire 31, through manipulation of the remote manual control, or thumb ring fitting 29, is positioned within the longitudinal channel 60 and advanced distally within the passageway, through the needle 41 and into the tracheal lumen. The guide wire is oscillated within the tracheal lumen by the manipulation of the thumb ring fitting 29. Further, manipulation of the guide wire by the operator confirms correct needle placement within the tracheal wall. Upon confirming correct placement of the needle 41, the thumb ring fitting is fully inserted into the frame of the surgical device which operatively releases the needle latch 140, allowing the retraction of the needle 41 into the distal portion of the elongated member 14. (see FIGS. 25–27). To retract the needle, the thumb ring fitting is disposed toward the handle such that a portion of the thumb ring contacts the camming surface of the needle latch. This contact with the camming surface of the needle latch causes the trigger end to be disposed upward thereby disengaging the needle bushing and permitting the spring urge the needle bushing away from the distal end of the elongated member and draw the needle bushing, needle driver and needle to the left, as shown in FIGS. 25 and 26.

As shown in FIG. 26, with the needle retracted, the thumb ring may still be disposed through a range of motion substantially defined by the length of the keyway. This allows for subsequent oscillation of the guide wire, while always maintaining at least 1 cm of the guide wire extending beyond the dilator tip in the tracheal lumen.

Thus, the needle is used to establish communication with the tracheal lumen, the aspiration mechanism then confirms intraluminal placement. After needle retraction, the flexible guide wire maintains the path and through oscillation the wire reconfirms dilator tip placement in an open space Thus, in accordance with the novel method for performing a tracheostomy of the present disclosure, the inflatable dilator 30 is employed with an inflatable or expandable cuff 28 along the tracheostomy tube 26 disposed on the elongated member 14, imparting significant advantages over conventional tracheostomy methods. For example, alternative percutaneous tracheostomy approaches require a separate obturator to hold the tracheostomy tube. Additional manipulation of the aspiration chamber by the operator can further reconfirm the position of the surgical device.

As shown in FIGS. 28 and 29, after the retraction of the retractable needle 41 from the tracheal wall, the dilator tip 68 is advanced through the tracheal wall such that a substantial portion of the inflatable dilator 30 is disposed in the tracheal wall. The inflatable dilator 30, depicted as a collapsed bag may be made from any suitable material able to be inflated and maintained rigidly under pressure. Most preferably the inflatable dilator comprises polyethylene terephthalate (PET). Once the inflatable dilator 30 is inserted into the tracheal wall, the surgeon depresses trigger 22 in the direction indicated by the directional arrow to selectively inflate inflatable dilator 30, as shown in FIG. 29. As the expandable dilator 30 inflates, the adjacent tracheal rings are displaced from each other to define the enlarged space shown in FIG. 29. FIGS. 30 and 31 illustrate the inflation of the inflatable dilator 30 by the downward movement of the piston 98 to push fluid 220 out of pump fluid reservoir 218 and into the fluid passageway to inflate the inflatable dilator. The dilator 30 is coaxially mounted about the distal end portion of the balloon mount 200. The preferred inflatable expandable dilator 30 can withstand an internal pressure of about and often in excess of 200 psi; the result being an expandable dilator having extraordinary radial expansion capabilities. Such radial expansion is in strong contrast to the inward pressure required by serial mechanical dilators used in known percutaneous tracheostomy kits. A suitable balloon or inflatable dilator for this expandable dilator device has been specially manufactured by Advanced Polymers, Inc. of Salem, Mass. While the expandable dilator of the present invention is preferably inflated by a fluid, especially a sterile saline fluid, it is contemplated that other fluids or gases, including inert fluids and gases could be pumped into the dilator. While gases could theoretically be used, gases compress more easily under pressure than do liquids and so would not ordinarily be preferred. While an inflatable dilator is particularly preferred, the present invention further contemplates an expandable dilator, able to expand via mechanical or other mechanisms alone or in conjunction with fluid or air pressure, as would be apparent to one skilled in the expanding device field.

The outer tracheostomy tube may be made from any suitable medical material able to be sterilized and is preferably packaged for single, disposable use. The tracheostomy tube preferably has an inflatable segment, or cuff that can be inflated by a fluid or gas, preferably air or an inert gas supplied under pressure.

It is contemplated that the apparatus of the present invention incorporates an elongated member dimensioned to properly engage tracheostomy tubes having industry standard dimensions. Similarly, the materials selected for use in connection with the apparatus of the present invention may be any material able to withstand impact and which can be sealed and contain fluid and air passageways as would be readily understood by those in the medical device field. Particularly preferred are the high impact plastics and stainless steel metal fittings that can withstand necessary preliminary sterilization protocols.

The pump in this embodiment is prefilled with fluid. It is further contemplated that, with modification, the apparatus of the present invention could be shipped and stored with fluids absent, and such fluids filled by the operator just prior to use. As shown in FIG. 32, after inflating the inflatable dilator 30 and creating the passageway through the tracheal wall, the surgical device is further inserted down the tracheal lumen.

At this point, the expandable dilator which is preferably an inflatable dilator is contracted, or partially contracted or deflated and the apparatus releases from the tracheostomy tube. The tracheostomy tube is held in place as the apparatus is pulled from the patient's neck. The expandable cuff of the trachea tube is then inflated, preferably by an external air supply. Once the cuff is inflated, the trachea tube will remain in position within the trachea.

If the operator desires to reposition the dilator tip after the needle has been retracted, the apparatus is preferably removed from the patient's neck prior to resetting the needle. To reset the needle, and dispose it into the extended position, a resetting tool is disposed through a reset aperture extending from the back of handle. The reset tool engages the reset cap and disposes the reset cap, needle bushing, needle driver and needle toward the distal end of the elongated member (to the extended position). This compresses the spring. As the thumb ring fitting is disposed to preclude contact with the camming surface of the needle latch, the trigger end is urged downward by tension bar acting against the housing. As the reset tool pushes the reset cap and needle retraction mechanism toward the distal end, the trigger end of the needle latch passes over the end of the needle bushing and a portion of the trigger end contacts the needle bushing to preclude motion of the needle bushing toward the left as shown in FIGS. 25 and 26, thus resetting the needle to the extended position. This allows the thumb ring fitting to withdraw back fully, thereby pulling the guide wire past the dilation tip and into the elongated member.

Apparatus 10 of the present disclosure provides significant advantages over conventional balloon catheter systems. Handle 12 is operable with a single hand of the operator, thus, freeing the operator's other hand to perform other functions. Due to the mechanical advantages provided through the trigger 22 and connected pump, the force required on behalf of the operator to expand the expandable dilator is greatly minimized. Further, the concentric mounting of expandable dilator about elongated member 14 provides for radial expansion of the expandable dilator, therefore, resulting in dilation of the tissue structure.

The operation of the apparatus is further simplified by the presence of a retractable needle which is moveable between a first position extending from the distal portion and a second position within the distal portion of the elongated member. Further, the inclusion of a tube, preferably a tracheostomy tube, disposed on the elongated member allows the operator to create an aperture in the trachea wall and insert the tracheostomy tube with a single surgical device.

Thus, in accordance with the novel method for performing a tracheostomy of the present disclosure, the expandable dilator is employed to provide an enlarged opening between the adjacent tracheal rings to permit insertion of a tracheostomy tube. The use of the apparatus of ther present invention with the expandable dilator has significant advantages over conventional tracheostomy methods. In accordance with conventional methods for performing a tracheostomy, dilating tubes of varying increasing sizes are forcibly inserted into an opening in the trachea to gradually enlarge the opening. This often requires a significant amount of force on behalf of the operator to insert the dilating tubes. Furthermore, forcing the dilating tubes inwardly into the trachea increases the potential of damaging the back wall of the trachea and other structures behind the trachea (e.g. esophagus, spine, etc.). However, with the apparatus of the present invention, the expandable dilator of the apparatus is easily positioned without requiring high insertion forces. Thereafter, the expandable dilator is expanded to perform gradual radial dilation and expansion of the adjacent tracheal rings.

It is understood that the entire procedure, designed to be conducted efficiently at bedside, can, with training take about one minute or less to complete from skin incision to tracheostomy tube cuff inflation. In addition, the lubrication ordinarily required in connection with equipment used for alternative percutaneous tracheostomy using serial mechanical dilators is not required with the device of the present invention. This makes the present device easier to handle for the operator and makes the entire procedure safer and more accurately reproducible. The present invention, therefore facilitates the multiple medical needs of providing greater patient comfort, efficiency, safety, etc. by providing fast, reliable, reproducible and therefore predictable positioning of a tracheostomy tube in a patient.

The following examples serve only to further illustrate aspects of the present invention and should not be construed as limiting the invention.

EXAMPLE 1

Preferred Tracheostomy Procedure Protocol

The following protocol for the preferred percutaneous tracheostomy procedure is done most easily with the right-handed operator standing to the left of the patient, or with the left-handed operator standing to the right of the patient. The patient's trachea is inspected and palpated to identify the desired tracheostomy target site along the anterior midline between the first and second trachea rings. A local anesthetic is injected into the skin and subcutaneous tissue and about the cartilaginous rings at the target site. A horizontal full thickness skin incision of about 1 to about 2 cm in length is made in the standard fashion using a scalpel. The operative site is immobilized by holding the trachea between the gloved thumb and index finger of the operator's non-dominant hand. The device of the present invention is picked up in the operator's dominant hand. The needle at its tip is then placed through the skin incision and into the underlying tissue above the trachea. The needle proceeds through the anterior midline of the trachea usually between the first and second cartilaginous rings until the resistance from the dilation tip is felt. The aspiration bulb is then depressed. Proper placement of the needle tip within the tracheal lumen is confirmed. If the aspiration bulb reinflates rapidly after the index finger is released, the needle tip is in the lumen of the trachea. A guide wire connected to the thumb ring is oscillated in and out of the end of the instrument about 1 cm. An easily sliding guide wire indicates proper placement. The thumb ring fitting is then pushed all the way into the instrument to retract the needle. The instrument is then rotated while advancing the device further until the shoulder of the balloon mounting member impedes advancement through the wall of the trachea. The collapsed inflation dilator is thus positioned in the opening of the tracheal wall. The trigger is then squeezed completely, infusing and expanding the inflation dilator. The opening into the trachea is thereby enlarged to a diameter slightly exceeding the diameter of tracheostomy tube. The device is inserted further into the lumen until the flange of the tracheostomy tube abuts the patient's neck. The trigger is then released, thus allowing the inflation dilator to deflate. The tracheostomy tube is then held in place while the device is withdrawn from the tracheostomy tube and removed from the patient's neck. The air intake tube of the tracheostomy tube is unwound from the flange and attached to a syringe. Air from the syringe is then injected into intake tube to inflate the tracheostomy tube cuff.

EXAMPLE 2

Twenty-five sheep heads amputated at the shoulders were obtained from animals previously slaughtered for meat at a slaughter house. Fifty percutaneous placements of standard 8 mm internal diameter tracheostomy tubes were performed. In each neck, a scalpel was used to make a 1 to 2 cm horizontal incision through the skin overlying the cricothyroid membrane. The balloon dilator device of the present invention was then used to create a cricothyroidotomy and place a tracheostomy tube. After removing the first tracheostomy tube, the technique was repeated in the same neck, except this time through a vertical skin incision over the first and second tracheal cartilages. Finally, the anterior midline of each trachea was opened. Each operative site was inspected and graded (i.e. none/superficial/penetration) for procedure related trauma. The mean time to complete each procedure from initiation of skin incision to tracheostomy tube cuff inflation was 36.1 seconds (standard deviation 12.6, ranging from 21.4 to 86.9 seconds). The mean times required for cricothyroidotomy (31.7 seconds, standard deviation 8.9) and tracheostomy (40.5 seconds, standard deviation 14.3) intubations were not statistically different. All tracheostomy tube placements were successful. No iatrogenic injuries occurred.

While the above description contains many specifics, these specifics should not be construed as limitations on the scope of the invention, but merely as an exemplification of a preferred embodiment thereof. Those skilled in the art will envision other possible variations that are within the scope and spirit of the invention as defined by the claims appended hereto.

What is claimed:

1. An apparatus for performing a one-handed percutaneous tracheostomy comprising:
   a hollow needle;
   a bulb connected to the needle for aspirating air though an end of the needle;
   a flexible guide wire extending through the needle;
   a fitting on one end of the guide wire for permitting the guide wire to be reciprocated with one of a user's hands that holds the instrument, from a retracted position substantially within the needle, to an extended position in which a substantial length of the guide wire extends beyond an end of the needle;
   an expandable dilator attached to the dilation tip for dilating a patient's tracheal wall when the dilator is expanded; and
   a tracheostomy tube detachably mounted with respect to the dilator for placement into a patient's tracheal lumen.

2. The apparatus according to claim 1, wherein the needle is retractable.

3. The apparatus according to claim 2, wherein the needle is coupled to the fitting and is retracted by applying force to the fitting.

4. The apparatus according to claim 1, further comprising a dilation tip disposed coaxially with respect to the guide wire and at a distal end of the expandable dilator.

5. The apparatus according to claim 1, wherein the expandable dilator comprises an inflatable dilator.

6. The apparatus according to claim 5, wherein the inflatable dilator is mechanically crimped to the apparatus at one end of the inflatable dilator.

7. The apparatus according to claim 5 further comprising a frame and an elongated member defining a longitudinal bore for permitting passage of a length of guide wire therethrough.

8. The apparatus according to claim 7, wherein the longitudinal bore defines a longitudinal passageway for reception and passage of the needle and the guide wire.

9. The apparatus according to claim 7, including a mounting mechanism for mounting the inflatable dilator to the elongated member, the mounting mechanism comprising a crimp ring at least partially positionable at the distal portion of the elongated member, the ring securely wedging an end portion of the expandable dilator in a fluid tight manner against a surface of the elongated member.

10. The apparatus according to claim 5, wherein the elongated member comprises an inflation fluid channel.

11. The apparatus according to claim 10, wherein the inflation fluid channel comprises at least one inflation aperture extending through an outer wall thereof in fluid communication with the expandable dilator, the one inflation aperture permitting inflation fluid to pass into and inflate the expandable dilator.

12. The apparatus according to claim 1, comprising a trigger.

13. The apparatus according to claim 12, further comprising a drive member connected at one end thereof to the trigger and at another end thereof to a pump of a fluid dispenser, the drive member moveable in response to movement of the trigger to cause corresponding reciprocal movement of a pump within the chamber.

14. The apparatus according to claim 13, wherein the drive member is at least partially accommodated within a channel defined in the frame, the drive member reciprocally axially movable within the channel.

15. The apparatus according to claim 14, wherein the expandable dilator is coaxially mounted with respect to the elongated member.

16. In an apparatus for performing a one-handed tracheostomy, the improvement for locating a patient's tracheal lumen comprising:
   a needle extending from the apparatus for insertion through the tracheal wall into a patient's tracheal lumen;
   a resilient guide wire extending through the needle;
   a fitting on a proximal end of the guide wire for engagement with one hand used to grip the apparatus; and
   a manually operable bulb operable by the same one hand while gripping the apparatus coupled to the needle for aspirating air through the needle for determining whether an end of the needle is located in a patient's tracheal lumen or in the patient's tracheal wall.

17. The apparatus according to claim 16, wherein the needle is retractable and also comprising a resilient guide wire extending through the needle;
   a fitting on a proximal end of the guide wire for engagement with one hand of a user used to grip the apparatus; and
   a distal end of the guide wire extendable into a patient's trachea for determining, by reciprocal movement of the guide wire, when the distal end of the wire is positioned in the a patient's tracheal lumen for guiding a tracheostomy tube into a patient's tracheal lumen.

18. The apparatus according to claim 17, wherein the guide wire comprises a curved distal end.

19. In an apparatus for performing a one-handed tracheostomy, the improvement for guiding a tracheostomy tube into a patient's tracheal lumen comprising:
   a handle;
   a resilient guide wire having a fitting on a proximal end extending from the handle for engagement with one hand of a user, used to grip the apparatus and a distal end extendible into a patient's trachea for determining, by reciprocal movement of the guide wire, when the distal end of the wire is positioned in a patient's tracheal lumen.

20. The apparatus according to claim 19, wherein the guide wire comprises a curved distal end.

21. A method for performing a one-handed percutaneous tracheostomy comprising:
   inserting a hollow needle through a tracheal wall with the one hand;
   deflating a bulb with the one hand to aspirate air through the needle to verify that the needle is within the lumen of a trachea;
   extending a guide wire from an end of the needle with the one hand;
   retracting the needle from the trachea while leaving the guide wire in place;
   extending an expandable dialator over the guide wire into the tracheal wall;
   expanding the dialator with the one hand to dilate the tracheal wall; and
   sliding the dilator and a tracheostomy tube into the lumen of the trachea.

22. The method according to claim 21, comprising the step of oscillating the guide wire to ensure that it is in the lumen of the trachea.

23. The method according to claim 21, wherein the tracheostomy tube has an outside diameter about equal to or smaller than the diameter of the expandable dialator.

24. A method for performing a percutaneous tracheostomy comprising:
   inserting a hollow needle through a tracheal wall;
   aspirating air through the needle to verify that the needle is within the lumen of a trachea;
   extending a guide wire from an end of the needle;
   oscillating the guide wire to ensure that it is in the lumen of the trachea;
   retracting the needle from the trachea while leaving the guide wire in place;
   inserting an expandable dialator into the tracheal wall;
   expanding the dialator to dilate the tracheal wall;
   inserting a tracheostomy tube through the dilated tracheal wall into the lumen of the trachea;
   at least partially contracting the expandable dilator; and
   removing the dilator through the tracheostomy tube.

* * * * *